United States Patent
Bedau et al.

(10) Patent No.: US 11,892,445 B2
(45) Date of Patent: *Feb. 6, 2024

(54) DEVICES, SYSTEMS, AND METHODS OF USING SMART FLUIDS TO CONTROL TRANSLOCATION SPEED THROUGH A NANOPORE

(71) Applicant: Western Digital Technologies, Inc., San Jose, CA (US)

(72) Inventors: Daniel Bedau, San Jose, CA (US); Justin P. Kinney, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/643,398

(22) Filed: Dec. 8, 2021

(65) Prior Publication Data

US 2023/0176032 A1   Jun. 8, 2023

(51) Int. Cl.
*C12Q 1/68* (2018.01)
*G01N 33/487* (2006.01)

(52) U.S. Cl.
CPC .............. *G01N 33/48721* (2013.01)

(58) Field of Classification Search
None
See application file for complete search history.

(56) References Cited

U.S. PATENT DOCUMENTS

| 7,980,765 B2 | 7/2011 | Reitz et al. |
| 8,602,182 B2 | 12/2013 | Clair et al. |
| 10,676,782 B2 | 6/2020 | McRuer et al. |
| 10,995,373 B2 | 5/2021 | Predki et al. |
| 2006/0038328 A1 | 2/2006 | Lu et al. |
| 2006/0063171 A1* | 3/2006 | Akeson ............ G01N 33/48721 435/6.11 |
| 2008/0248561 A1 | 10/2008 | Golovchenko et al. |

(Continued)

FOREIGN PATENT DOCUMENTS

| CN | 107764994 A | 3/2018 |
| CN | 115219558 A | 10/2022 |

(Continued)

OTHER PUBLICATIONS

International Search Report and Written Opinion from PCT Application No. PCT/US2022/030484 (filed May 23, 2022), dated Oct. 19, 2022.

(Continued)

*Primary Examiner* — Aaron A Priest

(57) ABSTRACT

Disclosed herein are devices, systems, and methods for controlling a translocation speed of a molecule through a nanopore. In some embodiments, a speed-control device comprises at least one fluid-retaining surface, a fluid region, a field-responsive fluid coupled to the fluid-retaining surface and situated in the fluid region. In some embodiments, a system comprises the nanopore, the speed-control device, and a field generator for generating a magnetic or electric field across the fluid region. The viscosity of the field-responsive fluid is dependent on a magnitude of the magnetic or electric field across the fluid region and can be controlled by changing a magnitude of the magnetic or electric field across the fluid region.

25 Claims, 12 Drawing Sheets

(56) References Cited

U.S. PATENT DOCUMENTS

| | | | |
|---|---|---|---|
| 2011/0053284 A1* | 3/2011 | Meller | G01N 33/48721 506/13 |
| 2011/0155574 A1 | 6/2011 | Golovchenko et al. | |
| 2011/0223652 A1 | 9/2011 | Peng et al. | |
| 2011/0236984 A1 | 9/2011 | Sun et al. | |
| 2012/0193235 A1 | 8/2012 | Afzali-Ardakani et al. | |
| 2012/0258544 A1* | 10/2012 | Chen | B82Y 15/00 422/82.09 |
| 2013/0176563 A1* | 7/2013 | Ozawa | B82Y 5/00 356/301 |
| 2013/0344498 A1 | 12/2013 | Marziali et al. | |
| 2018/0298436 A1 | 10/2018 | Lei et al. | |
| 2019/0002971 A1* | 1/2019 | Koslover | C12Q 1/6869 |
| 2019/0096555 A1 | 3/2019 | Khalil et al. | |
| 2020/0096493 A1* | 3/2020 | Roorda | G01N 33/48721 |
| 2020/0191767 A1* | 6/2020 | Tabard-Cossa | G01N 33/48721 |
| 2020/0292521 A1 | 9/2020 | Xie et al. | |
| 2023/0176032 A1 | 6/2023 | Bedau et al. | |
| 2023/0176033 A1 | 6/2023 | Bedau et al. | |

FOREIGN PATENT DOCUMENTS

| | | |
|---|---|---|
| JP | 2018510329 A | 4/2018 |
| KR | 1020120117834 A | 10/2012 |
| KR | 1020190104795 A | 9/2019 |
| KR | 1020200027034 A | 3/2020 |

OTHER PUBLICATIONS

Wang, Ceming et al., "Slowing down DNA translocation through solid-state nanopores by edge-fieldleakage", Nature Communications, Jan. 8, 2021 (Online publication date), vol. 12, Article No. 140, Internalpp. 1-10.

A. Spaggiari, "Properties and applications of Magnetorheological fluids," Scilla 2012—The Italian research on smart materials and MEMS, 23 (2013) 57-61; DOI: 10.3221/IGF-ESIS.23.06.

Ángel Díaz Carral et al., "Deep learning for nanopore ionic current blockades," J. Chem. Phys. 154, 044111 (Jan. 2021); https://doi.org/10.1063/5.0037938.

Chan Cao and Yi-Tao Long, "Biological Nanopores: Confined Spaces for Electrochemical Single-Molecule Analysis," Acc. Chem. Res., Jan. 2018, 51, 331-341.

Chenyu Wen, "On Rectification of Ionic Current in Nanopores," Anal. Chem. Oct. 2019, 91, 14597-14604.

Farzin Haque et al., "Solid-State and Biological Nanopore for Real-Time Sensing of Single Chemical and Sequencing of DNA," Nano Today. Feb. 2013; 8(1): 56-74.

G. Bossis et al., "Magnetorheology: Fluids, Structures and Rheology," Springer-Verlag, Stefan Odenbach (Ed.): LNP 594, pp. 202-230, 2002.

Goto, Y., Akahori, R., Yanagi, I., & Takeda, K., "Solid-state nanopores towards single-molecule DNA sequencing," Journal of Human Genetics (Aug. 2019), doi:10.1038/s10038-019-0655-8.

James Sathya Kumar et al., "A review of challenges and solutions in the preparation and use of magnetorheological fluids," International Journal of Mechanical and Materials Engineering (2019) 14:13, https://doi.org/10.1186/s40712-019-0109-2.

Jeffrey Comer and Aleksei Aksimentiev, "DNA Sequence-Dependent Ionic Currents in Ultra-Small Solid-State Nanopores," Nanoscale. May 5, 2016; 8(18): 9600-9613. doi:10.1039/c6nr01061j.

K. Chen et al., "Nanopoare-Based DNA Hard Drives for Rewritable and Secure Data Storage," Nano Lett., Mar. 2020, 20, 3754-3760.

Laura Conde-Canencia, Lara Dolecek, "Nanopore DNA sequencing channel modeling," IEEE International Workshop on Signal Processing Systems, Oct. 2019, Cape Town, South Africa.

Lee, H.H., Kalhor, R., Goela, N. et al. Terminator-free template-independent enzymatic DNA synthesis for digital information storage. Nat Commun 10, 2383 (Jun. 2019). https://doi.org/10.1038/s41467-019-10258-1.

Masateru Taniguchi, "Selective Multidetection Using Nanopores," Anal. Chem. 2015, 87, 188-199 (published Nov. 2014).

P. Berger et al., "Preparation and Properties of an Aqueous Ferrofluid," Journal of Chemical Education, vol. 76 No. 7 Jul. 1999.

Pramod K. Khulbe, et al., "DNA translocation through α-haemolysin nano-pores with potential application to macromolecular data storage," Journal of Applied Physics 97, 104317 pp. 1-7 (May 2005). doi: http://dx.doi.org/10.1063/1.1905791.

Qi Lu et al., "Smart and Functional Conducting Polymers: Application to Electrorheological Fluids," Molecules, Nov. 2018, 23, 2854; doi:10.3390/molecules23112854.

Rufan Zhang et al., "Growth of Half-Meter Long Carbon Nanotubes Based on Schulz Flory Distribution," CS Nano 2013, 7, 7, 6156-6161, Publication Date:Jun. 27, 2013.

S. Binmazlan, "The Behaviour ofMagnetorheological Fluids in Squeezemode," School of Mechanical and Manufacturing Engineering, Faculty of Engineering and Computing, Dublin City University, Aug. 2008.

Stijn van Dorp et al., "Origin of the electrophoretic force on DNA in solid-state nanopores," Nature Physics, vol. 5, May 2009.

Victor Zhimov et al., "Nucleic acid memory," Nature Materials, vol. 15, Apr. 2016.

Wang, C., Sensale, S., Pan, Z. et al. Slowing down DNA translocation through solid-state nanopores by edge-field leakage. Nat Commun 12, 140 (Jan. 2021). https://doi.org/10.1038/s41467-020-20409-4.

Yu Zhen Dong et al., "Recent development of electro-responsive smart electrorheological fluids," Soft Matter, Apr. 2019, 15, 3473-3486.

Yuhui He et al., "Solid-state nanopore systems: from materials to applications," NPG Asia Materials, 13, 48 (Jun. 2021), https://doi.org/10.1038/s41427-021-00313-z.

Z. W. Pan et al., "Very long carbon nanotubes," Nature, vol. 394, Aug. 13, 1998.

"Developing nanopore technology for sequencing DNA in real time," Medical Science, Apr. 30, 2021.

Khulbe, Pramod & Mansuripur, Masud & Gruener, Raphael. (2005). DNA translocation through α-hemolysin nanopores with potential application to macromolecular data storage. Journal of Applied Physics. 97. 104317-104317.10.1063/1.1905791.

Ki-Ho Han and A. Bruno Frazier, "Paramagnetic capture mode magnetophoretic microseparator for high efficiency blood cell separations," Lab on a Chip, Issue 2, 2006.

Mingyan Gao et al., "Self-Assembly of DNA Molecules in Magnetic Fields," available at https://uobrep.openrepository.com/bitstream/handle/10547/625343/8-Self-Assembly+of+DNA+Molecules+in+Magnetic+Fields.pdf?sequence=2 at least by Mar. 27, 2023.

Morii, N., Kido, G., Suzuki, H., Nimori, S. and Morii, H., 2004. "Molecular chain orientation of DNA films induced by both the magnetic field and the interfacial effect." Biomacromolecules, 5(6), pp. 2297-2307.

Sally A. Peyman et al., "Diamagnetic repulsion—A versatile tool for label-free particle handling in microfluidic devices," Journal of Chromatography A, vol. 1216, Issue 52, Dec. 25, 2009, pp. 9055-9062.

Winkleman, A., Perez-Castillejos, R., Gudiksen, K.L., Phillips, S.T., Prentiss, M. and Whitesides, G.M., 2007. Density-based diamagnetic separation: devices for detecting binding events and for collecting unlabeled diamagnetic particles in paramagnetic solutions. Analytical chemistry, 79(17), pp. 6542-6550.

Yi, J., 2006. Emergent paramagnetism of DNA molecules. Physical Review B, 74(21), p. 212406.

Ying, YL., Hu, ZL., Zhang, S. et al. Nanopore-based technologies beyond DNA sequencing. Nat. Nanotechnol. 17, 1136-1146 (2022).

Yoshida, K., Ozawa, S., Yamamoto, I., Yamaguchi, M., Ogawa, K. and Takamasu, T., 2007. DNA electrophoresis under the gradient magnetic field. physica status solidi (a), 204(12), pp. 3918-3921.

International Search Report and Written Opinion from PCT App. No. PCT/US2022/030487 (filed May 23, 2022), dated Nov. 7, 2022.

* cited by examiner

DEVICES, SYSTEMS, AND METHODS OF USING SMART FLUIDS TO CONTROL TRANSLOCATION SPEED THROUGH A NANOPORE

BACKGROUND

Nucleic acids are negatively-charged polyelectrolytes with four monomers that are covalently bonded to form polymer chains. For deoxyribonucleic acid (DNA), the monomers are the nucleotides adenine (A), thymine (T), guanine (G), and cytosine (C). For ribonucleic acid (RNA), they are A, C, G, and uracil (U).

The use of biomolecules, including DNA, RNA, and proteins, to store data has been proposed due to the density, stability, energy-efficiency, and longevity of biomolecules. For example, a human cell has a mass of about 3 picograms and stores around 6.4 GB of information. The volumetric density of DNA is estimated to be 1,000 times greater than that of flash memory, and its energy consumption $10^8$ times less than that of flash memory. In addition, the retention time of DNA is significantly greater than that of electronic memory. Thus, DNA can store information reliably over time.

Information bits can be encoded into biomolecules, such as nucleic acid strands, using a variety of techniques. Once encoded, the biomolecules can later be read using a structure called a nanopore, which is a small hole, typically 1-2 nm in diameter and a couple of nanometers thick. There are two types of nanopore: biological (also referred to as protein) nanopores and solid-state nanopores. A biological nanopore is made from a pore material embedded in a lipid membrane. A solid-state nanopore is a nanoscale (e.g., nanometer-sized) opening in a synthetic membrane (e.g., SiNx, $SiO_2$, etc.).

A target biomolecule, such as a nucleic acid strand, in an electrolyte solution can be driven through a nanopore (biological or solid-state), primarily by electrophoresis, and read. A highly-focused external electric field applied transverse to and in the vicinity of the nanopore (e.g., by sensing electrodes used to read or detect the biomolecule) acts on a relatively short segment of the negatively charged biomolecule and directs it through the hole in the nanopore. FIG. 1 illustrates a nanopore 15 with a biomolecule 20 (e.g., a single-stranded DNA (ssDNA) molecule), passing through it. Two sensing electrodes 18 are situated near the nanopore 15 to sense the ionic current through the nanopore 15. The sensing electrodes 18 are typically connected to a voltage source (not illustrated), which supplies a voltage to the sensing electrodes 18.

As a molecule passes through a nanopore, the ions occupying the pore are excluded, which causes changes in the ionic current and/or electronic signal measured across the nanopore (e.g., using the sensing electrodes 18 on opposite sides of the nanopore), which can be observed and used to detect constituent parts of the biomolecule (e.g., nucleotides of a DNA strand). For example, as nucleic acid moves, or translocates, through the nanopore, different nucleotides cause different ionic current patterns. Specifically, the nucleotides cause distinct, measurable ionic current blockades, or current drops, as they pass through the nanopore. The current blockades can be recorded (e.g., using a current amplifier) and converted into digital signals (e.g., using an analog-to-digital converter). These current blockades, or patterns of them, can be used to distinguish between different nucleotides. For example, by analyzing the amplitudes, durations, frequencies, and shapes of the blockade events, various properties of the target molecule can be obtained.

The duration of each current blockade is dependent on the translocation or dwell time of the biomolecule passing through the nanopore. One challenge with using nanopores is that there is a trade-off between signal-to-noise ratio (SNR) and resolution. Specifically, at the voltages that provide adequate SNR for reading the biomolecule, the translocation speed of biomolecules due to electrophoresis is too high (and the dwell time too low) to provide the highest resolution desired. For example, when the biomolecule is ssDNA, at sufficient SNR for reading, the translocation speed is too high to allow changes in the ionic current due to single nucleotides to be resolved. Each nucleotide of ssDNA spends only on the order of 1 µs or less within the nanopore at the voltages used. In order to detect individual nucleotides, a high sampling rate is needed, which amplifies thermal noise and reduces the SNR. The dwell time per nucleotide should be on the order of between 100 µs and 1 ms to allow single-nucleotide resolution.

Therefore, there is a need for apparatuses and techniques that can control and/or reduce the translocation speeds of molecules through nanopores.

SUMMARY

This summary represents non-limiting embodiments of the disclosure.

In some aspects, the techniques described herein relate to a system for controlling a translocation speed of a molecule through a nanopore, the system including: a speed-control device including: at least one fluid-retaining surface, a fluid region, and a field-responsive fluid coupled to the at least one fluid-retaining surface and situated in the fluid region; and a field generator for generating a magnetic or electric field across the fluid region, wherein a viscosity of the field-responsive fluid is dependent on a magnitude of the magnetic or electric field across the fluid region.

In some aspects, the techniques described herein relate to a system, wherein the field generator includes at least one of a voltage source or a switch.

In some aspects, the techniques described herein relate to a system, further including: a speed detector configured to detect a speed of the molecule through the nanopore; a controller coupled to the speed detector and configured to: obtain, from the speed detector, an indication of the detected speed of the molecule through the nanopore, and provide, to the field generator, a control signal to adjust a magnitude of the magnetic or electric field across the fluid region based at least in part on the indication of the detected speed of the molecule through the nanopore.

In some aspects, the techniques described herein relate to a system, wherein the controller is further configured to compare the detected speed to a desired speed of the molecule through the nanopore.

In some aspects, the techniques described herein relate to a system, wherein the field-responsive fluid is an electrorheological fluid, and further including a first electrode and a second electrode, wherein at least one of the first electrode or the second electrode includes the at least one fluid-retaining surface.

In some aspects, the techniques described herein relate to a system, wherein the at least one fluid-retaining surface includes a material with an affinity for the electrorheological fluid.

In some aspects, the techniques described herein relate to a system, further including a shield situated between the nanopore and the first and second electrodes.

In some aspects, the techniques described herein relate to a system, wherein the field-responsive fluid is a magnetorheological fluid or a ferrofluid.

In some aspects, the techniques described herein relate to a system, further including a ferromagnetic yoke, wherein the ferromagnetic yoke includes a base.

In some aspects, the techniques described herein relate to a system, further including: a solenoid situated around the base of the ferromagnetic yoke, wherein the solenoid is coupled to a voltage source.

In some aspects, the techniques described herein relate to a system, further including: a hollow cylinder; and a solenoid situated around the hollow cylinder, wherein: an interior surface of the hollow cylinder includes the at least one fluid-retaining surface, and the solenoid is coupled to a voltage source.

In some aspects, the techniques described herein relate to a system, wherein the hollow cylinder includes a ferromagnetic material.

In some aspects, the techniques described herein relate to a system, further including the nanopore, wherein the speed-control device is situated on a leading side of the nanopore.

In some aspects, the techniques described herein relate to a system, wherein the speed-control device and the nanopore are adjacent.

In some aspects, the techniques described herein relate to a system, further including the nanopore, wherein the speed-control device is situated on a trailing side of the nanopore.

In some aspects, the techniques described herein relate to a system, wherein the speed-control device and the nanopore are adjacent.

In some aspects, the techniques described herein relate to a system for reading molecules, the system including: a plurality of fluid regions, each of the plurality of fluid regions containing a respective volume of field-responsive fluid, each of the plurality of fluid regions corresponding to a respective one of a plurality of nanopores; and at least one field generator, the at least one field generator configured to subject the plurality of fluid regions to one or more electric or magnetic fields.

In some aspects, the techniques described herein relate to a system, wherein the field-responsive fluid is an electrorheological fluid, and wherein the plurality of fluid regions is arranged in an array, and wherein each of the plurality of fluid regions is associated with a respective pair of electrodes coupled to the at least one field generator.

In some aspects, the techniques described herein relate to a system, wherein the field-responsive fluid is a magnetorheological fluid or a ferrofluid, and wherein the plurality of fluid regions is arranged in an array, and wherein each of the plurality of fluid regions is situated between a respective pair of pole pieces.

In some aspects, the techniques described herein relate to a system, wherein the plurality of fluid regions includes a first fluid region and a second fluid region, and wherein the first fluid region is situated between a first pole piece and a second pole piece, and wherein the second fluid region is situated between the second pole piece and a third pole piece.

In some aspects, the techniques described herein relate to a system, wherein each of the respective pair of pole pieces includes a ferromagnetic material.

In some aspects, the techniques described herein relate to a system, further including: a controller coupled to the at least one field generator and configured to adjust the one or more electric or magnetic fields based at least in part on a detected translocation speed.

In some aspects, the techniques described herein relate to a system, further including: a speed detector configured to detect a translocation speed and to provide an indication of the detected translocation speed to the controller.

In some aspects, the techniques described herein relate to a system, wherein the speed detector is configured to detect the translocation speed by recognizing a particular pattern in the molecule.

In some aspects, the techniques described herein relate to a system for controlling a speed of a molecule through a nanopore, the system including: means for holding a field-responsive fluid in a pathway of the molecule; means for generating a magnetic or electric field across the field-responsive fluid; means for detecting a translocation speed of the molecule through the nanopore; and means for adjusting the magnetic or electric field across the field-responsive fluid in response to the detected translocation speed.

Although the disclosure herein is largely in the context of controlling the translocation speed of biomolecules through a nanopore, it is to be understood that embodiments of the speed-control devices disclosed herein can also be used to control the speed of or grip non-biological or inorganic molecules.

In some aspects, the techniques described herein relate to a system for controlling movement of at least one molecule in a first fluid having a first viscosity, the system including: a fluid region defined by at least one fluid-retaining surface, wherein the fluid region is traversable by the at least one molecule; a field-responsive fluid situated in the fluid region; and a field generator for generating a magnetic or electric field across the fluid region, wherein, in response to a magnitude of the magnetic or electric field across the fluid region exceeding a threshold magnitude, a viscosity of the field-responsive fluid is greater than the first viscosity.

In some aspects, the techniques described herein relate to a system, wherein the field-responsive fluid is coupled to at least a portion of the at least one fluid-retaining surface.

In some aspects, the techniques described herein relate to a system, wherein the field generator includes a voltage source.

In some aspects, the techniques described herein relate to a system, further including: a speed detector configured to detect a speed of the at least one molecule through the fluid region; and a controller coupled to the speed detector and configured to: obtain, from the speed detector, an indication of the detected speed of the at least one molecule through the fluid region, and provide, to the field generator, a control signal to adjust a magnitude of the magnetic or electric field across the fluid region based at least in part on the indication of the detected speed of the at least one molecule through the fluid region.

In some aspects, the techniques described herein relate to a system, wherein the controller is further configured to compare the detected speed to a desired speed of the at least one molecule through the fluid region.

In some aspects, the techniques described herein relate to a system, wherein the field-responsive fluid is an electrorheological fluid, and further including a first electrode and a second electrode, wherein at least one of the first electrode or the second electrode includes the at least one fluid-retaining surface.

In some aspects, the techniques described herein relate to a system, wherein the at least one fluid-retaining surface includes a material with an affinity for the electrorheological fluid.

In some aspects, the techniques described herein relate to a system, wherein the field-responsive fluid is a magneto-rheological fluid or a ferrofluid.

In some aspects, the techniques described herein relate to a system, further including a ferromagnetic yoke, wherein the ferromagnetic yoke includes a base.

In some aspects, the techniques described herein relate to a system, further including: a solenoid situated around the base of the ferromagnetic yoke, wherein the solenoid is coupled to a voltage source.

In some aspects, the techniques described herein relate to a system, further including: a hollow cylinder; and a solenoid situated around the hollow cylinder, wherein: an interior surface of the hollow cylinder includes the at least one fluid-retaining surface, and the solenoid is coupled to a voltage source.

In some aspects, the techniques described herein relate to a system, wherein the hollow cylinder includes a ferromagnetic material.

In some aspects, the techniques described herein relate to a system, wherein the at least one molecule includes a non-biological or inorganic molecule.

In some aspects, the techniques described herein relate to a system, wherein the at least one molecule includes a carbon nanotube or a polymer molecule.

In some aspects, the techniques described herein relate to a method of controlling movement of at least one molecule, the method including: generating a magnetic or electric field across a fluid region situated in an apparatus, the fluid region containing a field-responsive fluid, wherein a viscosity of the field-responsive fluid is dependent on a magnitude of the generated magnetic or electric field; detecting a speed of the at least one molecule through the fluid region; and adjusting the magnitude of the magnetic or electric field based at least in part on the detected speed of the at least one molecule through the fluid region.

In some aspects, the techniques described herein relate to a method, further including: adding a fluid containing the at least one molecule to the apparatus.

In some aspects, the techniques described herein relate to a method, wherein adjusting the magnitude of the magnetic or electric field based at least in part on the detected speed of the at least one molecule through the fluid region includes adjusting the magnitude of the magnetic or electric field until the speed of the at least one molecule through the fluid region is substantially zero.

In some aspects, the techniques described herein relate to a system for controlling a speed of at least one molecule, the system including: a field-responsive fluid, wherein a property of the field-responsive fluid is responsive to an applied magnetic or electric field; means for holding the field-responsive fluid in a pathway of the at least one molecule; and means for generating the applied magnetic or electric field across the field-responsive fluid.

In some aspects, the techniques described herein relate to a system, further including: means for detecting the speed of the at least one molecule through the field-responsive fluid.

In some aspects, the techniques described herein relate to a system, further including: means for adjusting the applied magnetic or electric field across the field-responsive fluid in response to the detected speed.

In some aspects, the techniques described herein relate to a system, further including: means for directing the at least one molecule into the field-responsive fluid.

In some aspects, the techniques described herein relate to a system, wherein, in response to a magnitude of the applied magnetic or electric field exceeding a threshold, a viscosity of the field-responsive fluid is greater than a viscosity of a surrounding fluid.

In some aspects, the techniques described herein relate to a system, wherein the property of the field-responsive fluid is a viscosity of the field-responsive fluid.

BRIEF DESCRIPTION OF THE DRAWINGS

Objects, features, and advantages of the disclosure will be readily apparent from the following description of certain embodiments taken in conjunction with the accompanying drawings in which.

Figure 1:
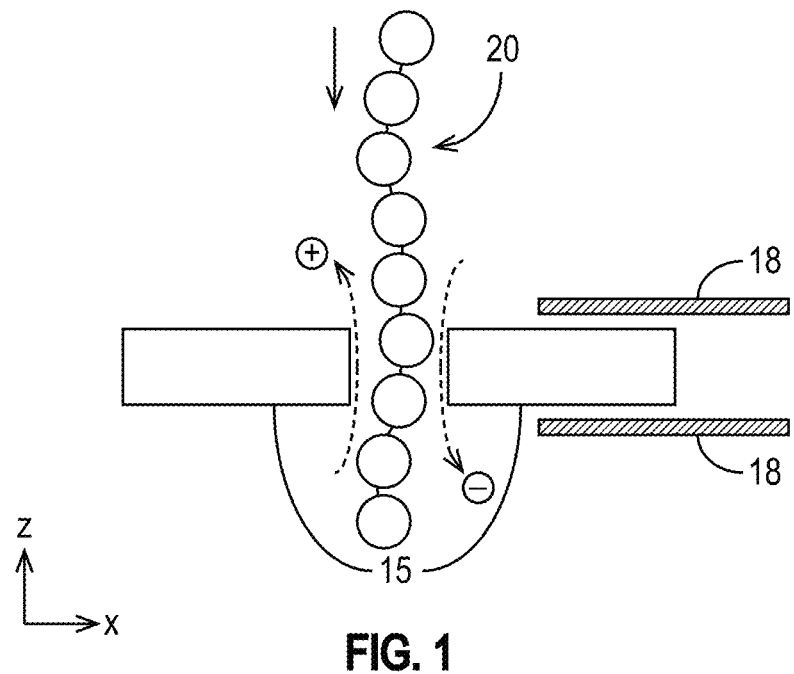
FIG. 1 illustrates a nanopore with a biomolecule passing through it.

To facilitate understanding, identical reference numerals have been used, where possible, to designate identical elements that are common to the figures. It is contemplated that elements disclosed in one embodiment may be beneficially utilized in other embodiments without specific recitation. Moreover, the description of an element in the context of one drawing is applicable to other drawings illustrating that element.

DETAILED DESCRIPTION

A number of approaches have been proposed to control the translocation of biomolecules through a nanopore. For example, one approach is to reduce the bias voltage provided to the sensing electrodes 18 to decrease the translocation speed. The result, however, is that decreasing the bias voltage decreases the sensed magnitude of the ionic current relative to thermal noise. Therefore, the SNR decreases. Reducing the bias voltage can also reduce throughput by reducing the rate at which biomolecules are drawn into the nanopore.

Other approaches proposed or attempted to reduce the translocation speed of molecules through a nanopore include modifying the properties of the electrolyte containing the molecules (e.g., adding salt, reducing the temperature, using glycerol rather than water, etc.), using traps or tweezers, or using protein tags. If successful, these methods are expected to result in only modest reductions in the translocation speed. Moreover, these approaches are not generally tunable. Stated another way, they are brute-force approaches that do not allow fine control over the translocation speed of molecules through a nanopore.

Disclosed herein are speed-control devices, apparatuses, and systems that allow the speed of molecules through a nanopore to be controlled. Also disclosed are methods of controlling the speeds of molecules through a nanopore.

The disclosed speed-control devices can be situated in the vicinity of or in contact with a nanopore. The disclosed speed-control devices include a fluid region that contains a field-responsive fluid, which may be, for example, an electrorheological (ER) fluid, a magnetorheological (MR) fluid, or a ferrofluid. The field-responsive fluid is held within the fluid region by at least one fluid-retaining surface. By applying an electric field (for ER fluid) or a magnetic field (for MR or fluid or ferrofluid) to the fluid region, the viscosity of the field-responsive fluid in the fluid region can be adjusted to create mechanical resistance and slow the translocation of biomolecules through an associated nanopore. The viscosity of the fluid-responsive fluid is dependent on the magnitude of the applied field. The at least one fluid-retaining surface can function only to hold the field-responsive fluid in place within the fluid region, or it can, in addition to holding the field-responsive fluid in place, assist in providing the electric or magnetic field. For example, the at least one fluid-retaining surface can be a surface of an electrode (for ER fluid) or a pole piece (for MR fluid or ferrofluid). A feedback signal that provides an indication of the translocation speed of biomolecules through the nanopore can be used to make rapid adjustments to the applied field in order to adjust or tune the viscosity of the field-responsive fluid and thereby adjust the translocation speed. For example, the field can be increased to reduce the translocation speed and decreased to increase the translocation speed. The adjustments can be made quickly due to the properties of the field-responsive fluid, the viscosity of which can be adjusted in milliseconds.

An array of nanopores and associated speed-control devices can be provided to allow a plurality of biomolecules to be read at the same time.

Field-responsive fluids, such as ER fluids, MR fluids, and ferrofluids, which are sometimes referred to as smart fluids, include a carrier liquid and solid particles. The characteristics of a field-responsive fluid are determined in part by the carrier liquid and particle size.

For ER fluids, the carrier liquid is typically an electrically insulating fluid, such as an oil, dielectric gel, or polymer. The particles in an ER fluid generally comprise fine, electrically polarizable but non-conducting particles (e.g., polymers, zeolites, etc.). The particles can be, for example, ferroelectric particles (e.g., particles with a spontaneous electric polarization that can be reversed by the application of an external electric field), conductors coated with an insulator, or electro-osmotically active particles. An ER fluid may also contain additives and/or surfactants. An ER fluid may comprise, for example, mobile charge carriers, such as polyacene quinines, polymetric electrolytes of Bayer, carbonaceous fluid of Bridgestone, zeolites, polyelectrolytes, etc.

When an ER fluid is subjected to an electric field, the particles become polarized, and the polarized particles bind together to form chains along the electric field lines. These chains restrict movement and cause the ER fluid to act more like a solid than a liquid. Thus, the viscosity of an ER fluid can be adjusted across a wide range (on the order of up to 100,000) in response to an applied electric field. For example, an ER fluid can go from a liquid state to a gel-like state within milliseconds, and then back to a liquid state within the same time frame.

The ER fluid is suspended in a fluid region between two field-generating electrodes. When an electric field is applied, the viscosity of the ER fluid will change. If no field is applied, the fluid will be mechanically held.

For MR fluids, the carrier liquid is a fluid that will not react with magnetic particles. Typically, the carrier liquid is water, mineral oil, silicone oil, or another synthetic oil with low viscosity. The particles in an MR fluid are magnetic (e.g., ferromagnetic, ferrimagnetic, etc.), and they are generally micro-meter-sized spheres or ellipsoids (e.g., between 0.1 and 10 micrometers in diameter). The magnetic particles may be, for example, iron particles. Because of the inherent difference in density between the magnetic particles of an MR fluid and the carrier liquid, the particles in an MR fluid tend to settle over time. Therefore, MR fluids may also include an additive (e.g., surfactants) to prevent agglomeration of the magnetic particles and/or to slow the rate at which the magnetic particles settle. Absent a magnetic field, and assuming little or no settling of particles, the magnetic particles are randomly distributed throughout and suspended within the carrier liquid.

Similarly to how ER fluids behave with respect to electric fields, MR fluids have low viscosity and behave like free-flowing liquids in the absence of an applied magnetic field, but they become flow resistant semi-solids with controllable yield strength in the presence of an applied magnetic field of sufficient strength. Specifically, when an MR fluid is subjected to an adequately-strong magnetic field, the particles align themselves in chains formed along the magnetic flux lines, thereby increasing the apparent viscosity of the MR fluid. By adjusting the intensity of the applied magnetic field (e.g., using an electromagnet), the viscosity of the MR fluid can be adjusted. As for ER fluids, MR fluids have response times on the order of milliseconds, which allows rapid adjustments to the viscosity.

Ferrofluids are similar to MR fluids except that their particles are nanometer-sized (e.g., ferromagnetic or ferrimagnetic nanoparticles around 10 nm or smaller in diameter), and, as a result, ferrofluids do not retain magnetization in the absence of an applied magnetic field. Thus, ferrofluids can be referred to as superparamagnetic. The particles may be, for example, magnetite, manganese ferrite ($MnFe_2O_4$), cobalt ferrite ($CoFe_2O_4$), etc. Because the particles of a ferrofluid are so small, they tend to remain suspended in the carrier liquid by Brownian motion and, unlike the particles of an MR fluid, typically do not settle. To prevent clumping, the magnetic particles of a ferrofluid are typically coated with a surfactant. The carrier liquid of a ferrofluid is typically water or an organic solvent (e.g., oil, diester, etc.) in order to produce a stable colloidal suspension. For example, ferrofluids can use water, oil, or a liquid metal (e.g., mercury, gallium alloys).

Ferrofluids behave similarly to MR fluids. A sufficiently-strong applied magnetic field induces dipolar interactions within the magnetic particles, which causes them to align in the direction of the magnetic field, which increases the viscosity of the ferrofluid. Unlike MR fluids, however, ferrofluids can maintain their viscosity in the presence of higher-magnitude magnetic fields without the particles forming any chain.

Various of the systems, devices, and methods disclosed herein can use ER fluid, MR fluid, or ferrofluid, as explained further below.

Figure 2A:
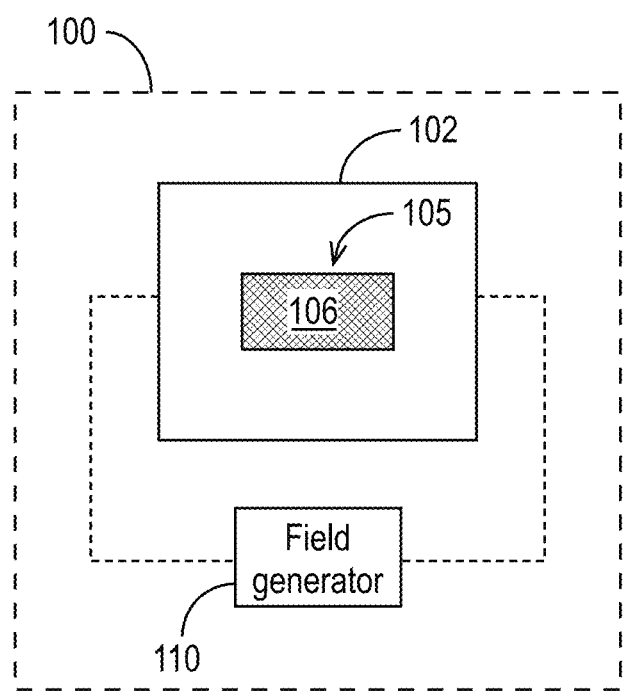
FIG. 2A is a diagram illustrating certain components of an example system in accordance with some embodiments.

FIG. 2A is a diagram illustrating certain components of an example system 100 in accordance with some embodiments. The example system 100 comprises at least one fluid-retaining surface 102, a fluid region 105 containing a field-responsive fluid 106, and a field generator 110. For convenience, the at least one fluid-retaining surface 102, fluid region 105, and field-responsive fluid 106 are sometimes collectively referred to herein as forming a speed-control device (see, e.g., FIGS. 5A, 6A, and 6B, and the discussions thereof). The field-responsive fluid 106 may be an ER fluid, MR fluid, or ferrofluid, some of the properties of which are discussed above. The at least one fluid-retaining surface 102 is configured to hold a field-responsive fluid 106 largely within the fluid region 105 (but not necessarily stationary therein, and not necessarily entirely therein). As will be appreciated by those having ordinary skill in the art, the at least one fluid-retaining surface 102 can use one or more of a number of mechanisms to hold the field-responsive fluid 106 within the fluid region 105. For example, the at least one fluid-retaining surface 102 can hold the field-responsive fluid 106 in place via one or more of surface tension, affinity, chemical functionalization (e.g., by deposing a chemical on the at least one fluid-retaining surface 102 so that the field-responsive fluid 106 will have a strong attachment to the at least one fluid-retaining surface 102), electrical attraction, magnetic attraction, or any other mechanism that can be used to hold small volumes of fluids in place. As described further below, the fluid region 105 may be partially or entirely defined by the at least one fluid-retaining surface 102.

The fluid region 105 is acted on by a field generator 110. The field generator 110 may generate an electric field (e.g., if the field-responsive fluid 106 is an ER fluid) or a magnetic field (e.g., if the field-responsive fluid 106 is an MR fluid or a ferrofluid). As explained further below, the field generator 110 can be, but is not required to be, physically coupled to the at least one fluid-retaining surface 102. In FIG. 2A, the broken lines between the field generator 110 and the at least one fluid-retaining surface 102 indicate that the field generator 110 may be physically coupled to the at least one fluid-retaining surface 102, or it may simply induce a field across the fluid region 105 that affects the field-responsive fluid 106.

As explained above, the at least one fluid-retaining surface 102 can be made from any suitable material and can have any suitable dimensions and properties to retain the field-responsive fluid 106 in the fluid region 105. In some embodiments, the at least one fluid-retaining surface 102 assists in applying and/or focusing the applied field. In some embodiments, the at least one fluid-retaining surface 102 merely holds the field-responsive fluid 106 in place substantially within the fluid region 105.

Figure 2B:
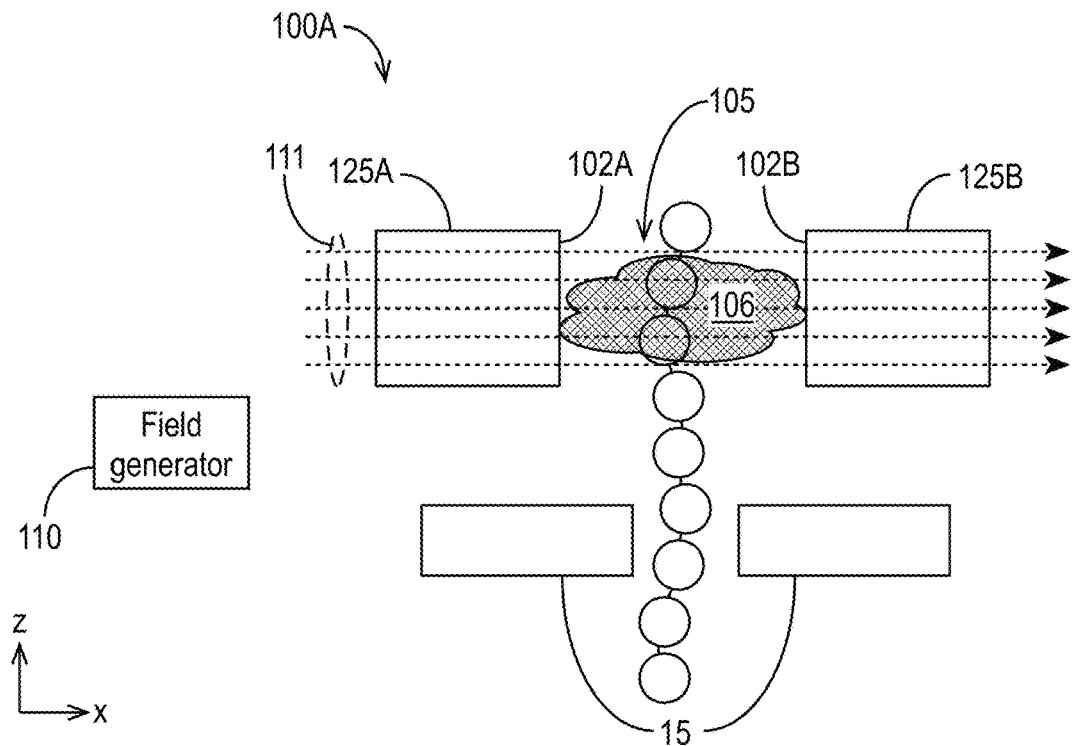
FIG. 2B illustrates portions of an example system in accordance with some embodiments.

FIGS. 2B through 2G illustrate several examples of configurations for fluid-retaining surfaces 102 in accordance with some embodiments. FIG. 2B illustrates portions of an example system 100A in accordance with some embodiments. The system 100A includes a first electrode 125A, a second electrode 125B, and a field generator 110. As shown, each of the first electrode 125A and second electrode 125B has a respective at least one fluid-retaining surface 102. Specifically, the first electrode 125A has a first fluid-retaining surface 102A, and the second electrode 125B has a second fluid-retaining surface 102B. Between the first fluid-retaining surface 102A and second fluid-retaining surface 102B is a fluid region 105, in which is a volume of field-responsive fluid 106. As explained above, the first electrode 125A, second electrode 125B, fluid region 105, and field-responsive fluid 106 together may be referred to as a speed-control device.

The system 100A also includes a field generator 110, which may comprise, for example, a voltage source as explained further below. In operation, the field generator 110 causes a field 111 to be generated between the first electrode 125A and second electrode 125B. The voltage source may be adjustable to allow the generated field to be adjusted. Thus, in the example system 100A of FIG. 2B, the first electrode 125A and second electrode 125B not only provide the at least one fluid-retaining surface 102, but they also assist in the application of the applied field.

As illustrated in FIG. 2B, in operation, the field generator 110 applies a field 111 that is perpendicular to the direction of travel of biomolecule 20. As described above, the presence of the field 111 increases the viscosity of the field-responsive fluid 106, which therefore increases the resistance encountered by biomolecule 20, thereby reducing its translocation speed. The field 111 can also direct (or assist to direct) the biomolecule 20 into the fluid region 105.

Figure 2C:
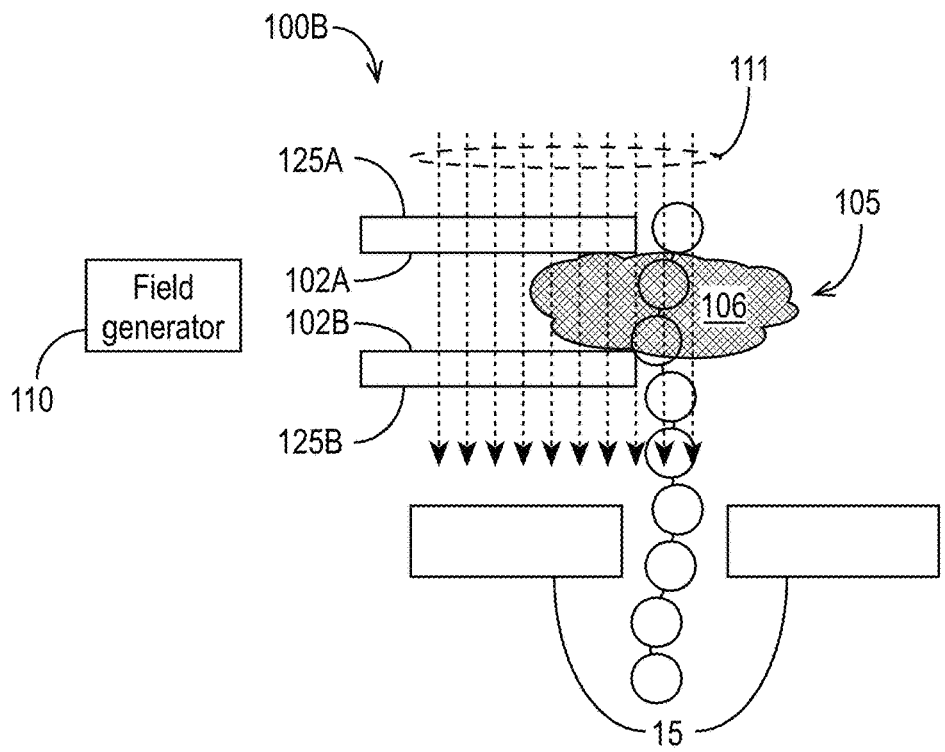
FIG. 2C illustrates portions of another example system in accordance with some embodiments.

FIG. 2C illustrates portions of another example system 100B in accordance with some embodiments. The system 100B includes a first electrode 125A, a second electrode 125B, and a field generator 110. As illustrated, each of the first electrode 125A and second electrode 125B has a respective at least one fluid-retaining surface 102. Specifically, the first electrode 125A has a first fluid-retaining surface 102A, and the second electrode 125B has a second fluid-retaining surface 102B. Between the first fluid-retaining surface 102A and second fluid-retaining surface 102B is a fluid region 105, in which is a volume of field-responsive fluid 106. As explained above, the first electrode 125A, second electrode 125B, fluid region 105, and field-responsive fluid 106 together may be referred to as a speed-control device. As shown in FIG. 2C, the fluid region 105 does not need to be entirely between the first electrode 125A and second electrode 125B. Specifically, the field-responsive fluid 106 can extend away from the first electrode 125A and second electrode 125B while still being held in place by the at least one fluid-retaining surface 102 (e.g., by surface tension, chemical functionalization, etc.).

The system 100B also includes a field generator 110, which may comprise, for example, a voltage source as explained further below. In operation, the field generator 110 causes a field 111 to be generated between the first electrode 125A and second electrode 125B. Thus, in the example system 100B of FIG. 2C, the first electrode 125A and second electrode 125B not only provide the at least one fluid-retaining surface 102, but they also assist in the application of the applied field.

As illustrated in FIG. 2C, in operation, the field generator 110 applies a field 111 that is parallel to the direction of travel of biomolecule 20. As described above, the presence of the field 111 increases the viscosity of the field-responsive fluid 106, which therefore increases the resistance encountered by biomolecule 20, thereby reducing its translocation speed.

It is to be appreciated that FIG. 2C is two dimensional, whereas an implementation of the system 100B is three-dimensional, and therefore, in an implementation of the system 100B, the first electrode 125A and second electrode 125B may be rotated relative to the positions in which they are illustrated in FIG. 2C. For example, the first electrode 125A and second electrode 125B can be rotated 90 degrees into or out of the page so that the fluid region 105 is substantially entirely between the first fluid-retaining surface 102A and second fluid-retaining surface 102B. Thus, the pathway of the biomolecule 20 can be between the first electrode 125A and second electrode 125B and not necessarily displaced to the sides of them as FIG. 2C might suggest. Those having ordinary skill in the art will appreciate that there are several ways to implement the system 100B in view of the disclosures herein.

The field-responsive fluid 106 in the system 100A and system 100B can be, for example, an ER fluid. The field-responsive fluid 106 can alternatively be a MR fluid or a ferrofluid, in which case the first electrode 125A and second electrode 125B can be replaced by pole pieces or yokes that can provide both the at least one fluid-retaining surface 102 and assist in applying a magnetic field.

Figure 2D:
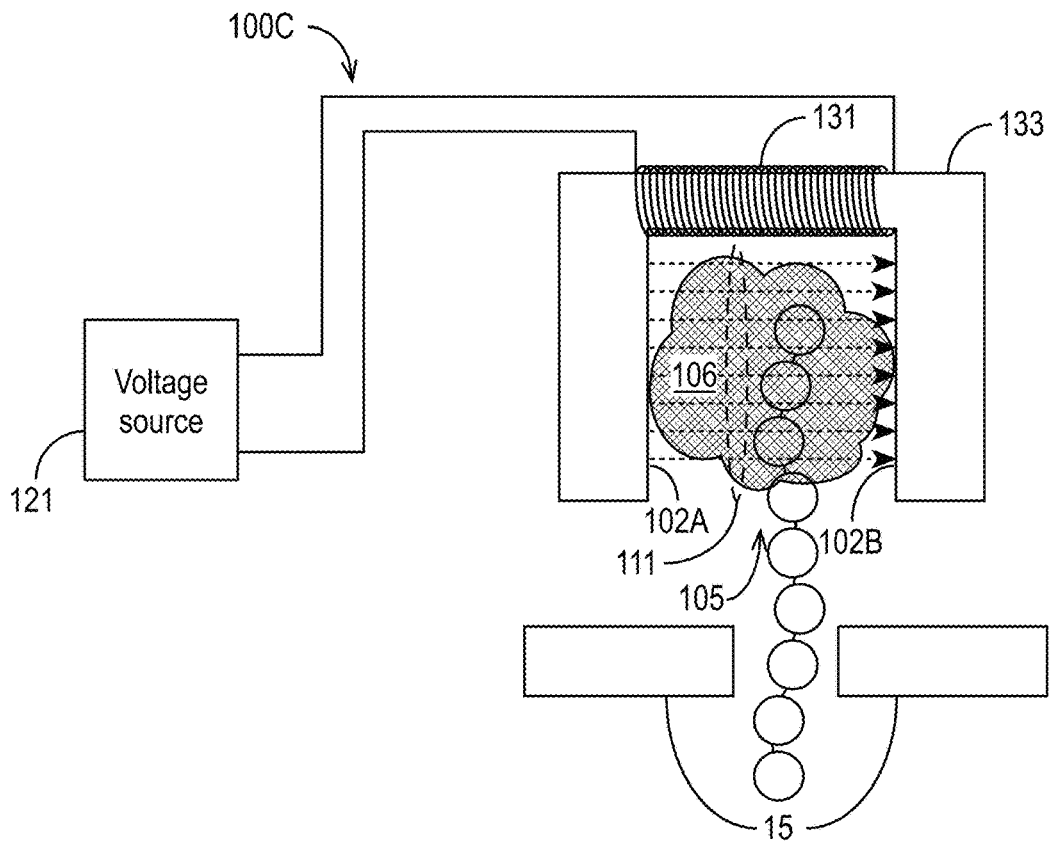
FIG. 2D illustrates portions of another example system in accordance with some embodiments.

For example, FIG. 2D illustrates an example of a system 100C that can use MR fluid or ferrofluid as the field-responsive fluid 106. The system 100C includes a yoke 133, including a base, a first leg, and a second leg, with a coil or solenoid 131 wrapped around the base of the yoke 133. The yoke 133 has at least one fluid-retaining surface 102. The yoke 133 of FIG. 2D has the first fluid-retaining surface 102A and second fluid-retaining surface 102B. The inner region of the yoke 133 (e.g., between the legs and the base) therefore at least partially defines the fluid region 105, which holds a volume of field-responsive fluid 106. The field-responsive fluid 106 may be MR fluid or ferrofluid. As explained above, the yoke 133, solenoid 131, fluid region 105, and field-responsive fluid 106 together may be referred to as a speed-control device.

The solenoid 131 is coupled to a voltage source 121. Accordingly, the combination of the yoke 133, solenoid 131, and voltage source 121 forms an electromagnet. In operation, and as illustrated in FIG. 2D, the voltage source 121, solenoid 131 and yoke 133 cause a field 111 (specifically, a magnetic field) to be generated between the legs of the yoke 133, in a direction perpendicular to the direction of travel of the biomolecule 20. The field 111 acts on the field-responsive fluid 106 and changes its viscosity. The presence of the field 111 increases the viscosity of the field-responsive fluid 106, which causes resistance to be applied to the biomolecule 20, which reduces its translocation speed through the nanopore 15. The voltage source 121 may be adjustable to allow the field 111 to be adjusted.

It is to be appreciated that FIG. 2D is two dimensional, whereas an implementation of the 100C is three-dimensional, and therefore yoke 133 and/or nanopore 15 may be rotated relative to the positions in which they are illustrated in FIG. 2D so the yoke 133 does not block the biomolecule 20 from entering the fluid region 105 and/or the nanopore 15. For example, the yoke 133 may be rotated 90 degrees into or out of the page so that the pathway of the biomolecule 20 is not blocked by the yoke 133. Those having ordinary skill in the art will appreciate how to implement the system 100C in view of the disclosures herein.

Figure 2E:
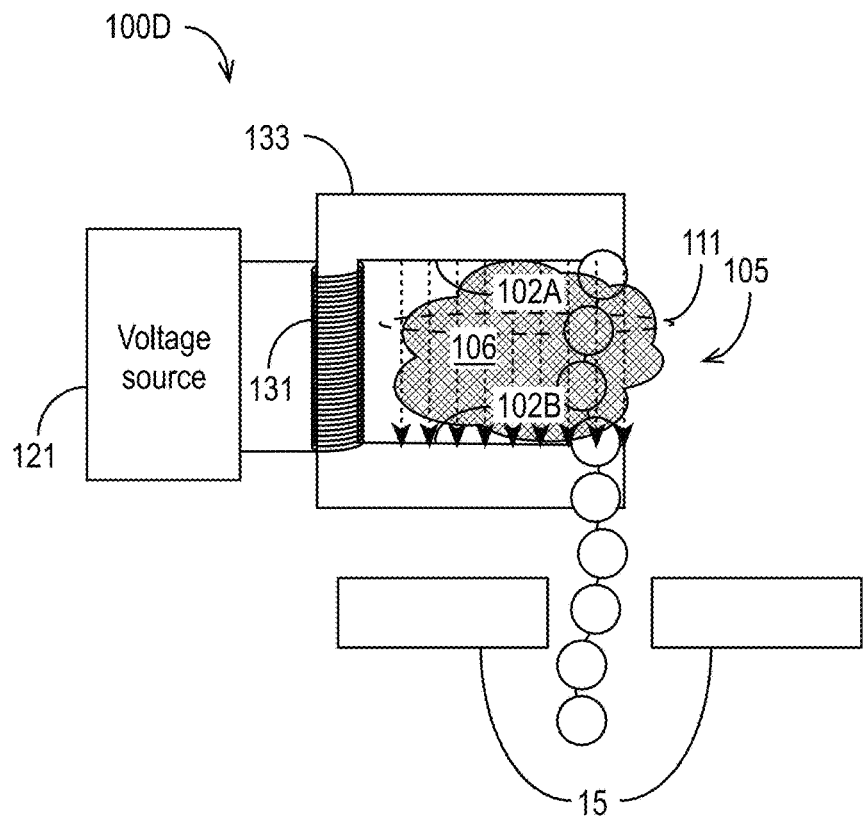
FIG. 2E illustrates portions of another example system in accordance with some embodiments.

FIG. 2E illustrates another example of a system 100D that can use MR fluid or ferrofluid as the field-responsive fluid 106. Like the system 100C, the system 100D includes a yoke 133 with a coil or solenoid 131 wrapped around the base of the yoke 133, and the solenoid 131 is coupled to a voltage source 121. The yoke 133 has a first fluid-retaining surface 102A (on a first leg) and a second fluid-retaining surface 102B (on a second leg). The inner region of the yoke 133 therefore at least partially defines the fluid region 105, which holds a volume of field-responsive fluid 106. The field-responsive fluid 106 may be MR fluid or ferrofluid. As explained above, the yoke 133, solenoid 131, fluid region 105, and field-responsive fluid 106 together may be referred to as a speed-control device.

As in the system 100C, the combination of the yoke 133, solenoid 131, and voltage source 121 forms an electromagnet. With the orientation of the yoke 133 illustrated in FIG. 2E, in operation, the (magnetic) field 111 is generated between the legs of the yoke 133 in a direction parallel to the direction of travel of the biomolecule 20. The voltage source 121 may be adjustable to allow the field 111 to be adjusted. As previously explained, the field 111 acts on the field-responsive fluid 106 and changes its viscosity, thereby causing resistance to be applied to the biomolecule 20, which reduces its translocation speed through the nanopore 15.

It is to be appreciated that FIG. 2E is two dimensional, whereas an implementation of the 100D is three-dimensional, and therefore the yoke 133 and/or nanopore 15 may be rotated relative to the positions in which they are illustrated in FIG. 2E so the fluid region 105 is more in line with the nanopore 15. For example, the yoke 133 can be rotated 90 degrees into or out of the page and shifted to the right of the page so that the fluid region 105 is substantially entirely between the first fluid-retaining surface 102A and second fluid-retaining surface 102B without any portion of the yoke 133 or solenoid 131 blocking the pathway of biomolecule 20. Thus, the pathway of the biomolecule 20 can be between the legs of the yoke 133. Those having ordinary skill in the art will appreciate that there are several ways to implement the system 100D in view of the disclosures herein.

Figure 2F:
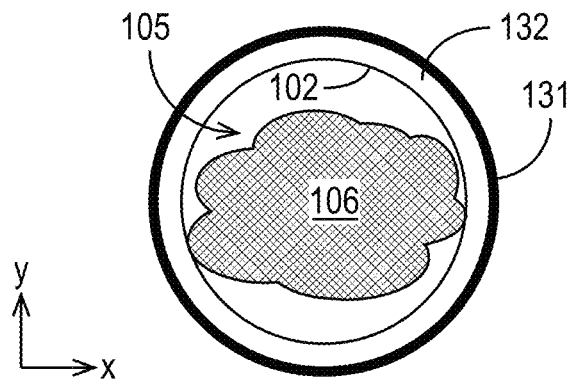
FIGS. 2F and 2G illustrate portions of another example system in accordance with some embodiments.
Figure 2G:
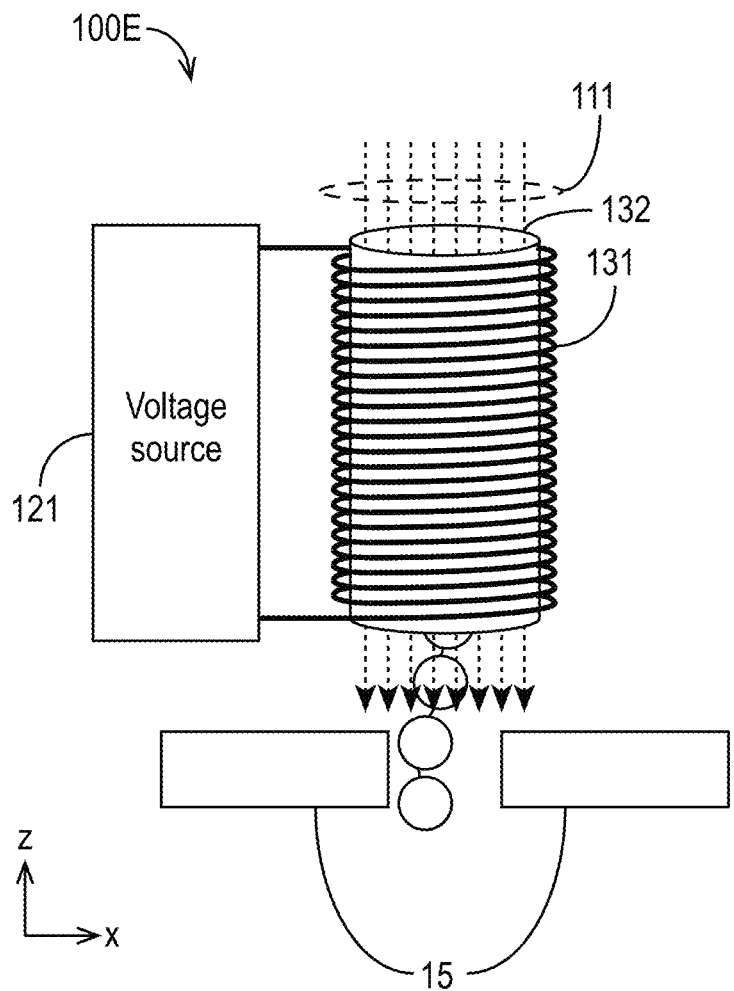

FIGS. 2F and 2G illustrate another example of a system 100E that can use MR fluid or ferrofluid as the field-responsive fluid 106. In the example embodiment shown in FIGS. 2F and 2G, a hollow cylinder 132 with a solenoid 131 around it is provided. The hollow cylinder 132 can be open at each end and situated such that a biomolecule 20 can pass through an interior of the hollow cylinder 132 and into the nanopore 15 (or can pass from the nanopore 15 into the hollow cylinder 132). The interior surface of the hollow cylinder 132 provides the at least one fluid-retaining surface 102 for the field-responsive fluid 106 in the fluid region 105. The hollow cylinder 132 may comprise a ferromagnetic material, such as iron. As explained above, the hollow cylinder 132, solenoid 131, fluid region 105, and field-responsive fluid 106 together may be referred to as a speed-control device. As shown in FIG. 2G, the solenoid 131 is coupled to a voltage source 121. The voltage source 121 may be adjustable to allow the generated field 111 to be adjusted.

As will be appreciated by those having ordinary skill in the art, the combination of the voltage source 121, solenoid 131, and hollow cylinder 132 forms an electromagnet. In operation, the (magnetic) field 111 is generated along the hollow cylinder 132 in a direction parallel to the direction of travel of the biomolecule 20. As previously explained, the field 111 acts on the field-responsive fluid 106 (an MR fluid or ferrofluid) and changes its viscosity, thereby causing resistance to be applied to the biomolecule 20, which reduces its translocation speed through the nanopore 15.

Although FIGS. 2D, 2E, 2F, and 2G illustrate particular components that can be used to generate a magnetic field, it is to be appreciated that there are many other ways to generate magnetic fields (e.g., generally by using an electromagnet or similar component(s)). The illustrations provided herein are merely exemplary and are not intended to be limiting. Other approaches are contemplated and are within the scope of the disclosures.

Each of FIGS. 2B, 2C, 2D, 2E, and 2F illustrates an example system 100 and a nanopore 15 to illustrate how the applied field can be oriented relative to the nanopore 15 and the direction of travel of the biomolecule 20. As discussed further below, a variety of relative positions of the speed-control device and the nanopore 15 are possible. Moreover, it should be appreciated that the nanopore 15 can be incorporated into and considered a part of the system 100, or it can be separate.

FIGS. 3A through 3D illustrate example systems that show how a speed-control device can be situated relative to a nanopore 15. The illustrated system 100 in FIGS. 3A through 3D is an example system 100 that includes a first electrode 125A and a second electrode 125B coupled to a field generator 110, but it is to be appreciated that the system 100 can be any system 100 that includes a field-responsive fluid 106, has at least one fluid-retaining surface 102, and a field generator 110 that, in operation, subjects the field-responsive fluid 106 to an applied field. In other words, the discussion of FIGS. 3A through 3D is not limited to systems 100 that use ER fluids. For example, the discussion of FIGS. 3A through 3D is applicable to all of the example embodiments of systems 100 described herein.

Figure 3A:
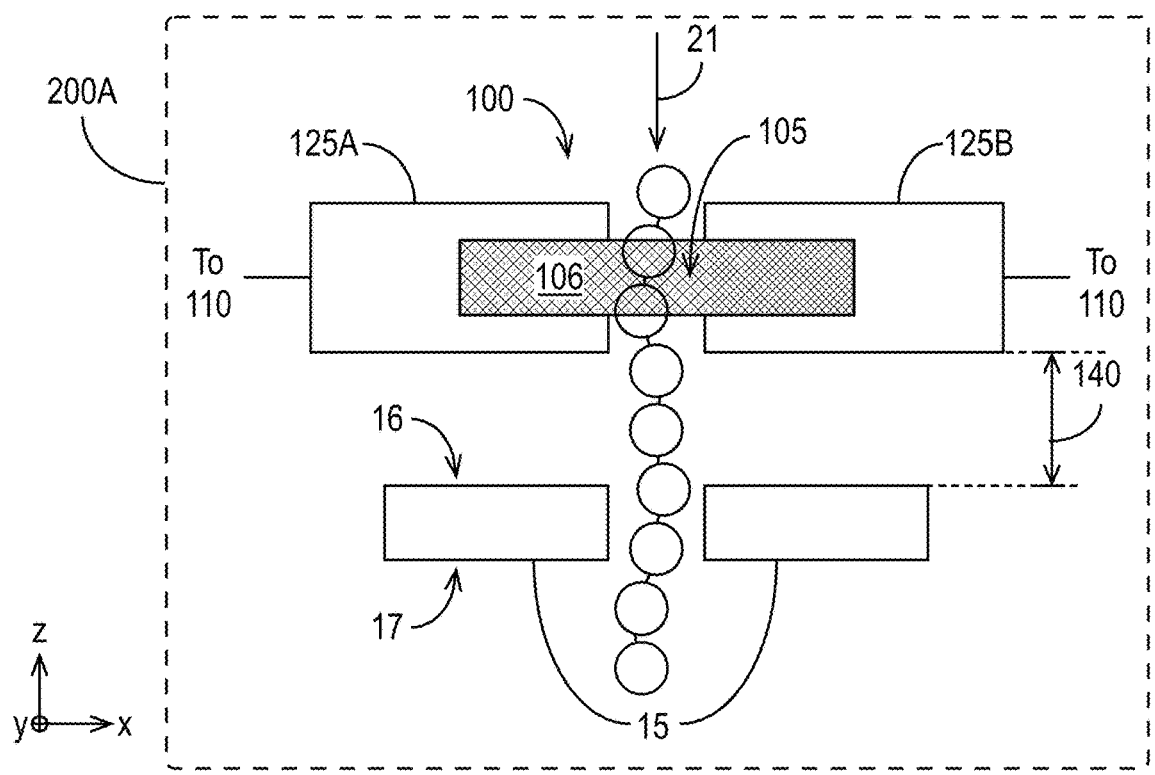
FIG. 3A is a diagram illustrating some components of an example system in which a speed-control device is situated in the vicinity of the leading side of a nanopore in accordance with some embodiments.

FIG. 3A is a diagram illustrating some components of an example system 200A in which an example speed-control device is situated in the vicinity of a nanopore 15 in accordance with some embodiments. FIG. 3A is a cross-sectional view of the example system 200A in an x-z plane. The nanopore 15 has a leading side 16 and a trailing side 17. As illustrated in FIG. 3A, the speed-control device is situated on the leading side 16 of the nanopore 15 and is offset from the nanopore 15 by a distance 140 in the z-direction.

In operation, assuming that biomolecule 20 travels in the direction of the arrow 21 (in the negative-z direction), biomolecule 20 enters the example speed-control device from the top of FIG. 3A. Assuming that the field generator 110 is generating a field of sufficient strength in the x-direction (perpendicular to the direction of travel of biomolecule 20), the presence of the field causes the viscosity of the field-responsive fluid 106 to increase. The increased viscosity of the field-responsive fluid 106 relative to the viscosity of the surrounding electrolyte causes biomolecule 20 to be delayed by the speed-control device. In a sense, the speed-control device acts as a "gripper" on biomolecule 20 as it passes through the speed-control device. Therefore, biomolecule 20 passes through the nanopore 15 at a reduced speed relative to what its translocation speed would have been absent the example system 100.

The distance 140 can be any suitable distance. For example, in the case that the field generator 110 generates an electric field, it may be desirable to choose the distance 140 so that the field 111 generated by the field generator 110 does not interfere substantially with the detection of the ionic current via the sensing electrodes 18. Regardless of the value of the distance 140, any coupling between an electric field generated by the field generator 110 and the sensing electrodes 18 can be taken into account when designing the system 200A.

Figure 3B:
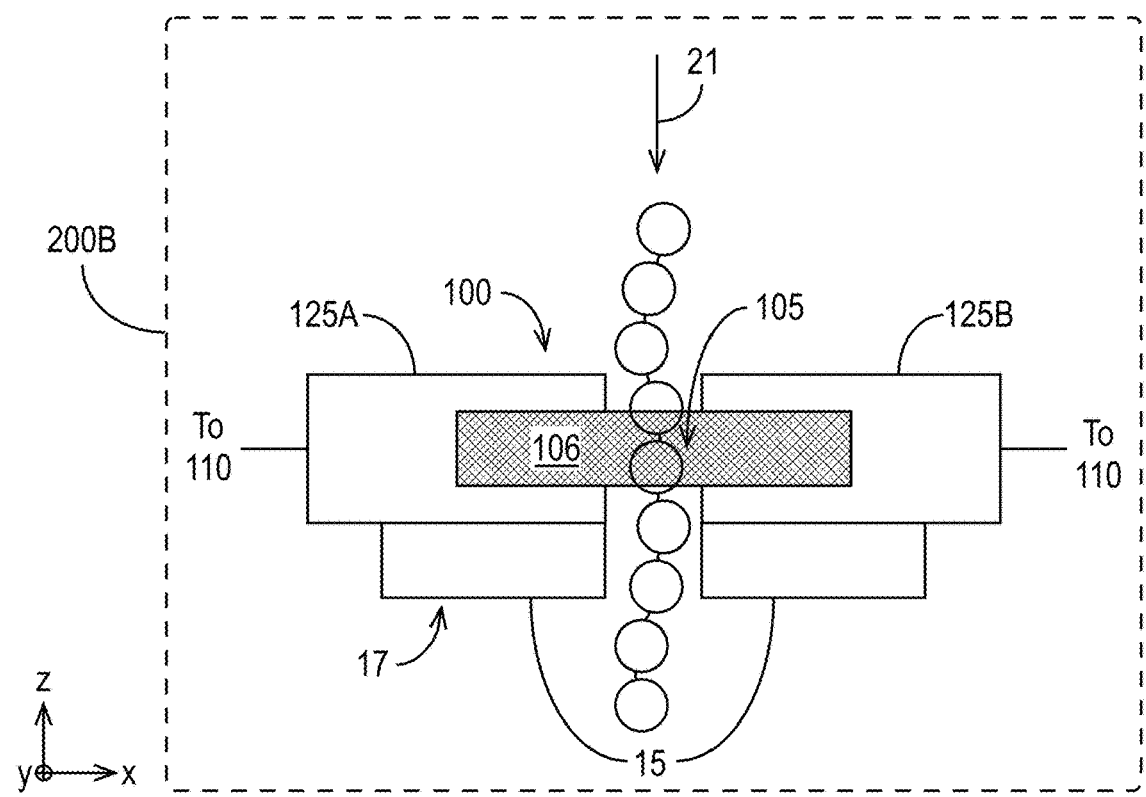
FIG. 3B is a diagram illustrating some components of an example system in which a speed-control device is situated adjacent to the leading side of a nanopore in accordance with some embodiments.

In some embodiments, the speed-control device is situated adjacent to (in contact with) the nanopore 15. FIG. 3B illustrates some example components of one such example system 200B in accordance with some embodiments. As shown in FIG. 3B, the speed-control device is situated adjacent to the nanopore 15 (e.g., the distance 140 is zero) on the leading side 16. In some embodiments in which the distance 140 is zero, the field generator 110 generates a magnetic field, and therefore situating the first fluid-retaining surface 102A and the second fluid-retaining surface 102B as shown in FIG. 3B should not have any appreciable impact on the ionic current measured through the nanopore 15. In some embodiments, the field generator 110 generates an electric field. In this case, a single voltage source can be used for both the speed-control device and to detect the ionic currents of the nanopore 15. Although the electric field used by the example system 100 may have an effect on the ionic current, that effect can be taken into account (e.g., considered to be an offset, which may be time-invariant or time-varying) when designing the system 200B. Thus, FIG. 3B illustrates that the speed-control device can be integrated with the nanopore 15.

Figure 3C:
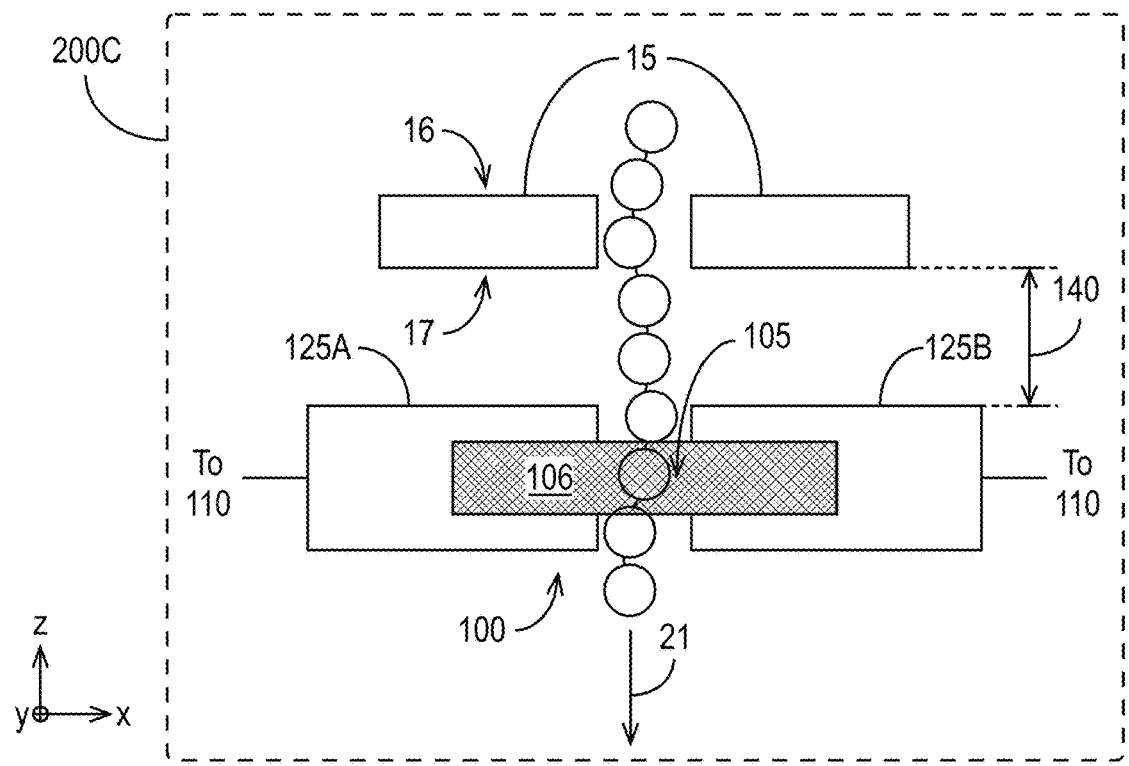
FIG. 3C is a diagram illustrating some components of an example system in which a speed-control device is situated in the vicinity of the trailing side of a nanopore in accordance with some embodiments.

FIG. 3C is a diagram illustrating some components of another example system 200C in which a speed-control device is situated in the vicinity of a nanopore 15 in accordance with some embodiments. Relative to the configuration of FIG. 3A, the speed-control device of FIG. 3C is on the other side of the nanopore 15. Specifically, the speed-control device is on the trailing side 17 of the nanopore 15. As illustrated in FIG. 3C, the speed-control device is offset from the trailing side 17 of the nanopore 15 by a distance 140 in the z-direction. As in the system 200A, the distance 140 in the system 200C can be any suitable distance, and any coupling into the sensing electrodes 18 that might occur due to the use of an electric field can be taken into account when designing the system 200C.

In operation, the system 200C operates similarly to the system 200A and system 200B. Assuming that biomolecule 20 travels in the direction of the arrow 21 (in the negative-z direction), biomolecule 20 first enters the nanopore 15 from the top of FIG. 3C, and then it enters the example speed-control device. Assuming that the field generator 110 is generating a field of sufficient strength, the increased viscosity of the field-responsive fluid 106 relative to the viscosity of the surrounding electrolyte causes biomolecule 20 to be delayed by the example system 100. In this case, the translocation speed of biomolecule 20 passing through the nanopore 15 will not be slowed by the speed-control device until its first part reaches the speed-control device. Therefore, in some embodiments, biomolecule 20 may have end portions that do not record information. For example, the first portion of biomolecule 20 may be a known sequence (e.g., of nucleotides) of sufficient length such that when the data-carrying portion of biomolecule 20 passes through the nanopore 15, the translocation speed of biomolecule 20 has been reduced relative to what its translocation speed would have been absent the example system 100. Because either end of biomolecule 20 can go through the nanopore 15 first, a dummy (e.g., non-data-storing) sequence can be added to both ends of biomolecule 20. Alternatively, or in addition, the first portion of biomolecule 20 may be a sequence that has properties to allow the speed of biomolecule 20 to be detected in a short amount of time. For example, the first portion of biomolecule 20 can be an easily-detected pattern such as an alternating and/or repeating pattern (e.g., 01010101 . . . or 001100110011 . . . , etc.). In the case that the biomolecule 20 is DNA or RNA, the pattern can be an easily-detectible pattern of A, T, C, and/or G (for DNA) (e.g., repeating sequences of one, two, or four bases), or an easily-detectible pattern of A, C, G, and U (for RNA).

Figure 3D:
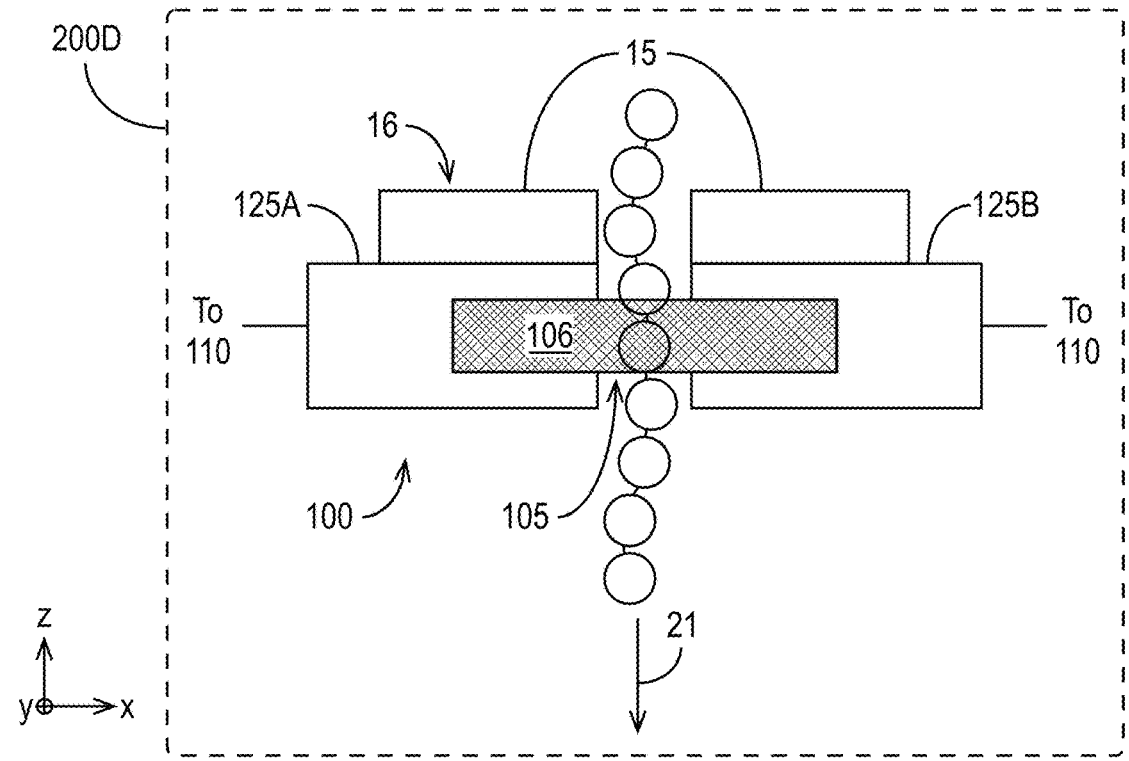
FIG. 3D is a diagram illustrating some components of an example system in which a speed-control device is situated adjacent to the trailing side of a nanopore in accordance with some embodiments.

Similarly to when the speed-control device is situated adjacent to the leading side 16 as shown in FIG. 3B and described above, the speed-control device can be situated adjacent to the trailing side 17 of the nanopore 15. FIG. 3D illustrates some example components of one such example system 200D in accordance with some embodiments. As shown in FIG. 3D, the speed-control device is situated adjacent to the trailing side 17 of the nanopore 15 (e.g., the distance 140 is zero). Thus, FIG. 3D illustrates that the speed-control device can be integrated with the nanopore 15. In this configuration, any dummy sequences added to the ends of biomolecule 20 can be shorter than when the distance 140 is nonzero. The discussion above in the context of FIG. 3B applies to FIG. 3D and is not repeated here.

In some embodiments in which the field-responsive fluid 106 is an electrorheological fluid, it may be desirable to include a shield to reduce interference to the nanopore 15 read signal due to electric fields caused by the field generator 110 (and first electrode 125A and second electrode 125B). For example, such a shield may reduce the effects of an AC field that might be generated in the event the voltage on the first electrode 125A and second electrode 125B changes quickly.

Figure 3E:
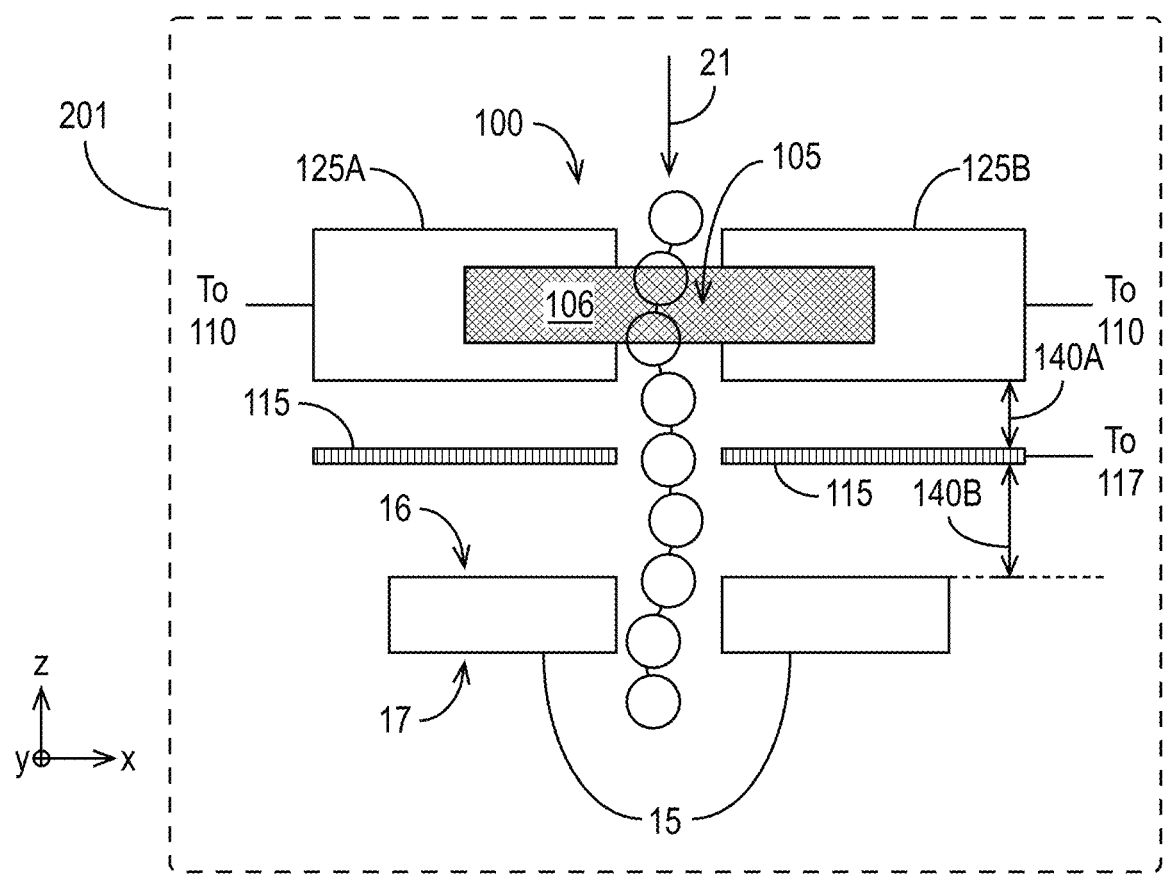
FIG. 3E illustrates a portion of an example system that includes a shield in accordance with some embodiments.

FIG. 3E illustrates a portion of an example system 201 that includes a shield 115 in accordance with some embodiments. As shown in FIG. 3E, the shield 115 is situated between the nanopore 15 and the first electrode 125A and second electrode 125B. In the illustration of FIG. 3E, the shield 115 is illustrated separated from the first electrode 125A and the second electrode 125B by a distance 140A, and it is separated from the nanopore 15 by a distance 140B. One or both of the distance 140A and the distance 140B can be zero, in which case a material or intervening layer may be included to electrically isolate the shield 115 from the first electrode 125A and second electrode 125B and/or the nanopore 15.

If included, the shield 115 may be made from any suitable material. For example, the shield 115 may comprise a conductive material, such as a metal, titanium nitride, or a similar material. The shield 115 may be fabricated as a layer deposited by, for example, physical vapor deposition (PVD).

Figure 3F:
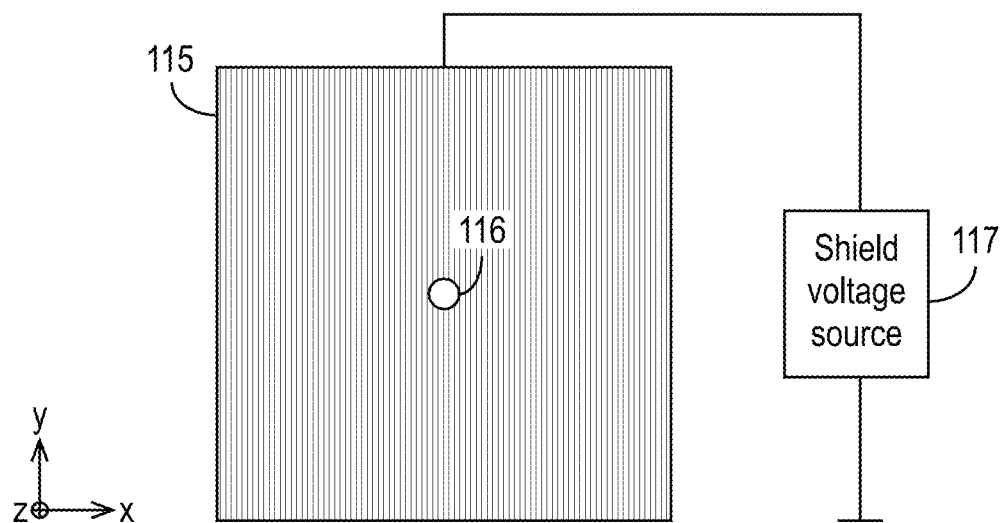
FIG. 3F illustrates an example shield in accordance with some embodiments.

FIG. 3F is a view of an example of the shield 115 in the x-y plane. As shown, the shield 115 can be, for example, a plate with a hole 116 to allow molecules to pass through. The hole 116 can be aligned with the fluid region 105 and/or the nanopore 15 (e.g., as shown in FIG. 3E). In the example of FIG. 3F, the shield 115 is coupled to a shield voltage source 117, which may be, for example, a defined potential (e.g., ground of a chip or device in which the system 201 resides) or an independent voltage source that can, for example, assist in threading the biomolecule 20 through the hole 116 in the shield 115 and directing it to the nanopore 15.

Figure 4A:
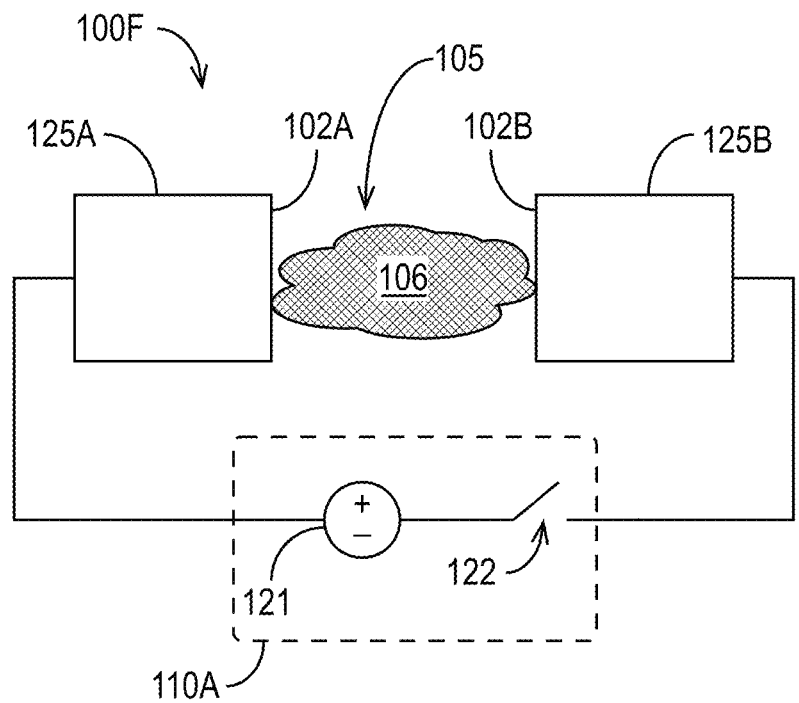
FIG. 4A illustrates components of an example system in accordance with some embodiments.

FIG. 4A illustrates components of an example system 100F that uses ER fluid as the field-responsive fluid 106 in accordance with some embodiments. The system 100F comprises a first electrode 125A with a first fluid-retaining surface 102A, a second electrode 125B with a second fluid-retaining surface 102B, and a fluid region 105 between the first fluid-retaining surface 102A and second fluid-retaining surface 102B as described above (e.g., in the discussion of FIG. 2B). Those descriptions apply to FIG. 4A and are not repeated here. Similarly, and as explained above, in combination, the first electrode 125A, second electrode 125B, fluid region 105, and the field-responsive fluid 106 together can be referred to as a speed-control device. The field-responsive fluid 106 in FIG. 4A is an ER fluid; therefore, its properties (e.g., viscosity) change in response to an electric field of sufficient magnitude. FIG. 4A also shows a field generator 110A comprising an adjustable voltage source 121 and a switch 122 in series with the voltage source 121. The system 100A is configured to generate an electric field between the first fluid-retaining surface 102A and second fluid-retaining surface 102B and thereby adjust the viscosity of the field-responsive fluid 106 (e.g., an ER fluid) in the fluid region 105. The switch 122 allows that applied field to be turned on (applied) and switched off.

It is to be appreciated that the example field generator 110A (the voltage source 121 and the switch 122) shown in FIG. 4A is merely an example of how an electric field can be generated between the first fluid-retaining surface 102A and second fluid-retaining surface 102B. Referring to the coordinate system used in FIGS. 3A-3D, the electric field is generated in the x-y plane. Other approaches are possible, are contemplated, and are within the scope of the disclosures herein. For example, as described above, the field 111 may be generated in another direction than perpendicular to the direction of motion of the biomolecule 20. It will be appreciated by those having ordinary skill in the art that applying a field 111 of sufficient magnitude to the field-responsive fluid 106 will cause the desired resistance to the biomolecule 20 and thereby allow its translocation speed through the nanopore 15 to be controlled.

Figure 4B:
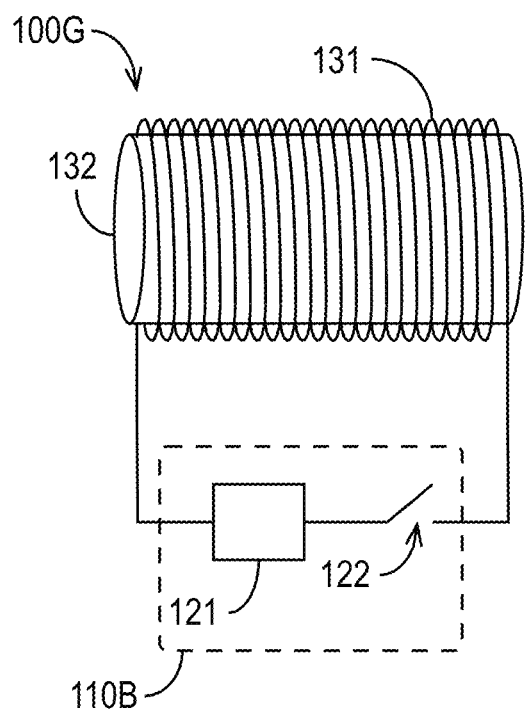
FIG. 4B illustrates components of another example system in accordance with some embodiments.

FIG. 4B illustrates components of another example system 100G that uses an MR fluid or ferrofluid in accordance with some embodiments. The system 100G comprises a solenoid 131 around a hollow cylinder 132 as described above in the discussion of FIGS. 2F and 2G. Those descriptions apply to FIG. 4B and are not repeated here. The field-responsive fluid 106 in FIG. 4B is responsive to a magnetic field; therefore, it may be an MR fluid or a ferrofluid. As explained above, in combination, the solenoid 131, hollow cylinder 132, fluid region 105, and field-responsive fluid 106 may be referred to as a speed-control device. FIG. 4B also shows a field generator 110B comprising a voltage source 121 and a switch 122. The voltage source 121 may be adjustable to allow the field 111 to be adjusted. The field generator 110B shown in FIG. 4B is physically connected to the solenoid 131. It is to be appreciated that in other embodiments, the field generator 110B need not be physically connected to other components of the speed-control device. For example, those having ordinary skill in the art will appreciate that a field generator 110B may be in the vicinity of, but not physically connected to, a speed-control device, such that a magnetic field generated by the field generator 110B influences the fluid region 105 within the hollow cylinder 132 and causes changes to the viscosity of the field-responsive fluid 106. Furthermore, although FIG. 4B shows a particular configuration for generating the field 111, it is to be appreciated that a magnetic field can be generated in alternative ways, some of which have been described herein (e.g., in the context of FIGS. 2D and 2E). Other approaches are possible, are contemplated, and are within the scope of the disclosures herein.

Figure 5A:
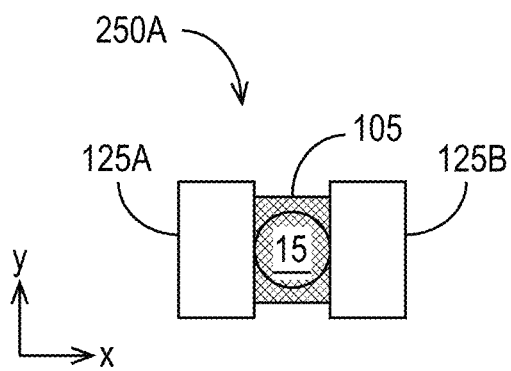
FIG. 5A is a view of a portion of an example device to control the translocation speed of biomolecules through a nanopore in accordance with some embodiments.

In some embodiments, a plurality of speed-control devices are arranged in an array. For example, FIG. 5A is a view of a portion of an example speed-control device 250A to control the translocation speed of biomolecules through a nanopore 15 in accordance with some embodiments. FIG. 5A is a plan view of the speed-control device 250A, either from above or below the speed-control device 250A, with the nanopore 15 outline shown for convenience. Using the coordinate system of FIGS. 3A-3D, the view in FIG. 5A is in the x-y plane. The speed-control device 250A comprises a pair of electrodes, shown in FIG. 5A as a first electrode 125A and a second electrode 125B with a fluid region 105 between them (e.g., between a first fluid-retaining surface 102A and a second fluid-retaining surface 102B). The fluid region 105 is shown with field-responsive fluid 106 (not labeled). The field-responsive fluid 106 is an ER fluid. The nanopore 15, which may be adjacent to the first electrode 125A and second electrode 125B or separated from them by a distance 140 in the z-direction (see FIGS. 3A-3D), is illustrated as having a round shape in the x-y plane, but the nanopore 15 can have any suitable shape. Likewise, although the first electrode 125A and second electrode 125B are represented as being rectangular in the x-y plane, they can have any suitable shape and dimensions.

In operation, the speed-control device 250A applies (e.g., assists the field generator 110 to apply) an electric field largely in the x-direction between the first electrode 125A and second electrode 125B, which alters the viscosity of the field-responsive fluid 106 (e.g., an ER fluid). (As explained above, it is to be appreciated that the field 111 can be in another direction, such as the y-direction or the z-direction, or some arbitrary direction.) A biomolecule 20 traveling through the nanopore 15 (in the direction into or out of the page) will thus encounter more resistance when traversing the field-responsive fluid 106, which will reduce its translocation speed relative to when the electric field 111 is absent.

Figure 5B:
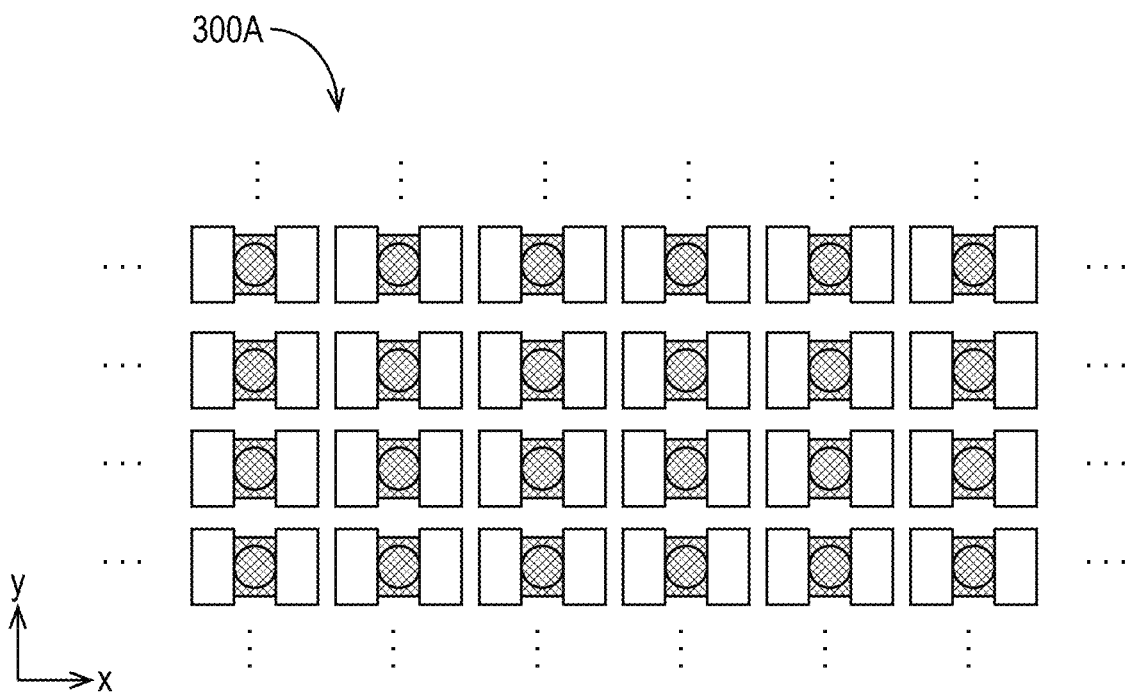
FIG. 5B is a diagram of an example array of speed-control devices in accordance with some embodiments.

Multiple substantially-identical instances of the speed-control device 250A can be incorporated into a system that includes an array of nanopores. FIG. 5B illustrates an example array 300A that includes multiple instances of the speed-control device 250A shown in FIG. 5A and discussed above. FIG. 5B shows 24 instances of the speed-control device 250A (and 24 nanopores), but it is to be appreciated that the array 300A can have more or fewer of the speed-control device 250A (and more or fewer corresponding nanopores). To avoid obscuring the drawing, neither the individual speed-control devices 250A nor the component parts of the speed-control devices 250A are labeled in FIG. 5B.

Each of the speed-control devices 250A in the array 300A can be provided a dedicated field generator 110, or multiple speed-control devices 250A can share a field generator 110. In the case that multiple speed-control device 250A share a field generator 110, individual or subsets of speed-control device 250A can be coupled to circuitry to allow finer tuning of the field 111.

Figure 6A:
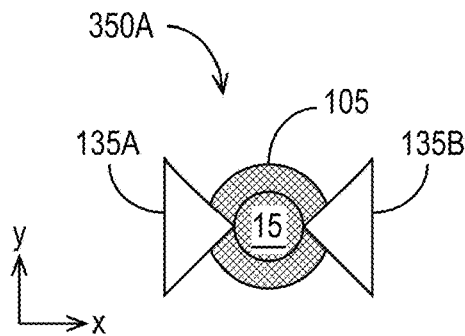
FIG. 6A is a view of a portion of an example device to control the translocation speed of biomolecules through a nanopore in accordance with some embodiments.

FIG. 6A is a view of a portion of another example speed-control device 350A to control the translocation speed of biomolecules through a nanopore in accordance with some embodiments. FIG. 6A is a plan view, either from above or below the speed-control device 350A. Using the coordinate system of FIGS. 3A-3D, the view in FIG. 6A is in the x-y plane. The speed-control device 350A comprises a pair of pole pieces, shown as a first pole piece 135A and a second pole piece 135B with a fluid region 105 between them. The fluid region 105 is shown with field-responsive fluid 106 (not labeled), which in this case is MR fluid or ferrofluid. The first pole piece 135A and second pole piece 135B may be, for example, yokes of an electromagnet, and they may have a shape configured to focus the magnetic field in a desired or particular direction. The first pole piece 135A and second pole piece 135B may comprise a magnetic material, such as iron, so that the field-responsive fluid 106 is attracted to (e.g., sticks to) the first pole piece 135A and second pole piece 135B, even in the absence of a magnetic field. Thus, the first pole piece 135A and second pole piece 135B may provide the first fluid-retaining surface 102A and second fluid-retaining surface 102B.

The nanopore 15, which may be adjacent to the first pole piece 135A and second pole piece 135B or separated from them by a distance 140 in the z-direction (see FIGS. 3A-3D), is illustrated as having a round shape in the x-y plane, but the nanopore 15 can have any suitable shape. Likewise, although the first pole piece 135A and second pole piece 135B are illustrated as being triangular in the x-y plane, they can have any suitable shape and dimensions.

In operation, the speed-control device 350A applies a magnetic field between the first pole piece 135A and second pole piece 135B, which modifies the viscosity of the field-responsive fluid 106 (e.g., an MR fluid or a ferrofluid). A biomolecule 20 traveling through the nanopore 15 (in the direction into or out of the page) will thus encounter more resistance when traversing the field-responsive fluid 106, which will reduce its translocation speed relative to when the magnetic field is absent.

Figure 6B:
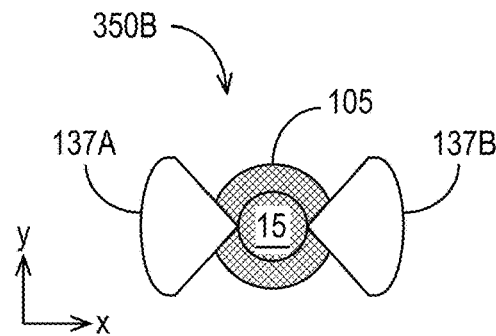
FIG. 6B is a view of a portion of another example device to control the translocation speed of biomolecules through a nanopore in accordance with some embodiments.

FIG. 6B is a view of a portion of another example speed-control device 350B to control the translocation speed of biomolecules through a nanopore in accordance with some embodiments. The speed-control device 350B is similar to the speed-control device 350A of FIG. 6A, but it includes a first pole piece 137A and a second pole piece 137B that have different shapes than the first pole piece 135A and second pole piece 135B. Like the first pole piece 135A and the second pole piece 135B, the first pole piece 137A and second pole piece 137B may be, for example, yokes of an electromagnet, and they may have a shape configured to focus the magnetic field in the desired direction. The first pole piece 137A and second pole piece 137B may comprise a ferromagnetic material, such as iron, so that the field-responsive fluid 106 is attracted to (e.g., sticks to) the first pole piece 137A and second pole piece 137B, even in the absence of an applied magnetic field. Thus, the first pole piece 137A and second pole piece 137B may provide the first fluid-retaining surface 102A and second fluid-retaining surface 102B.

The nanopore 15, which may be adjacent to the first pole piece 137A and second pole piece 137B or separated from them by a distance 140 in the z-direction (see FIGS. 3A-3D), is illustrated as having a round shape in the x-y plane, but the nanopore 15 can have any suitable shape. Likewise, although the first pole piece 137A and second pole piece 137B are illustrated as having a particular shape, they can have any suitable shape and dimensions.

In operation, the speed-control device 350B applies a magnetic field between the first pole piece 137A and second pole piece 137B, which modifies the viscosity of the field-responsive fluid 106 (e.g., an MR fluid or a ferrofluid). A biomolecule 20 traveling through the nanopore 15 (in the direction into or out of the page) will thus encounter more resistance when traversing the field-responsive fluid 106, which will reduce its translocation speed relative to when the magnetic field is absent.

Figure 6C:
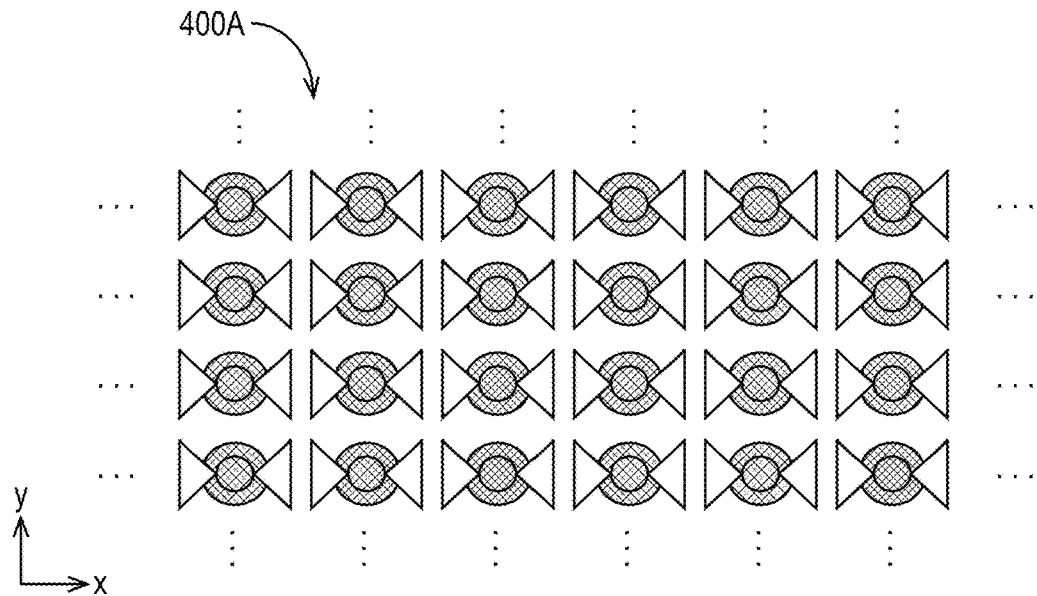
FIG. 6C is a diagram of an example array of speed-control devices in accordance with some embodiments.
Figure 6D:
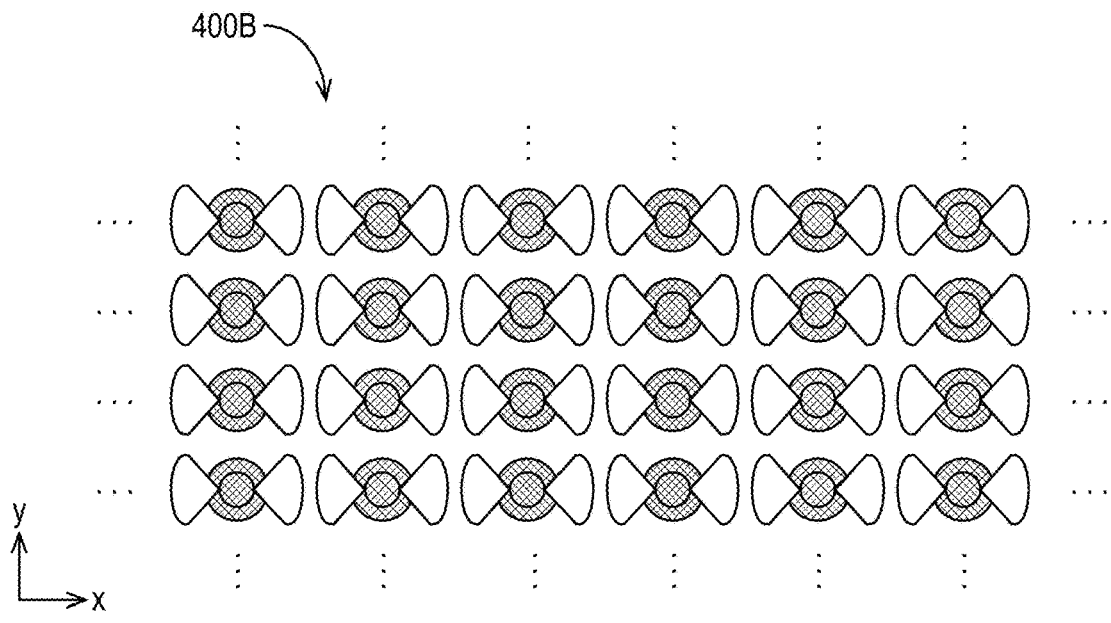
FIG. 6D is a diagram of another example array of speed-control devices in accordance with some embodiments.

Multiple instances of the speed-control device 350A or the speed-control device 350B can be incorporated into a system that includes an array of nanopores. FIG. 6C illustrates an example array 400A that includes multiple instances of the speed-control device 350A shown in FIG. 6A and discussed above, and FIG. 6D illustrates an example array 400B that includes multiple instances of the speed-control device 350B shown in FIG. 6B and discussed above. FIGS. 6C and 6D show 24 nanopores and 24 instances of, respectively, the speed-control device 350A and speed-control device 350B, but it is to be appreciated that the array 400A and the array 400B can have more or fewer of, respectively, the speed-control device 350A and the speed-control device 350B (and more or fewer corresponding nanopores). To avoid obscuring the drawings, neither the individual speed-control devices 350A, 350B nor the component parts of the speed-control devices 350A, 350B are labeled in FIGS. 6C and 6D.

Figure 6E:
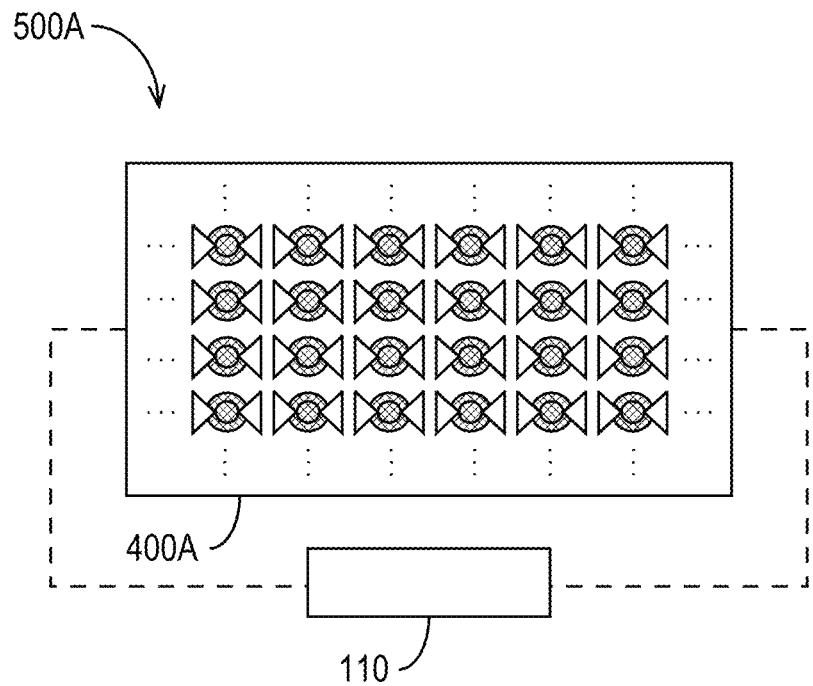
FIG. 6E is an illustration of an example system using an array in accordance with some embodiments.

Each of the speed-control devices 350A in the array 400A and each of the speed-control device 350B in the array 400B can be provided a dedicated field generator 110, or multiple speed-control devices 350A, 350B can share a field generator 110. For example, in some embodiments, a single field generator 110 is used to subject a plurality of the speed-control devices 350A (or speed-control device 350B) in the array 400A (or the array 400B) to a field generated by a single field generator 110. As an example, a single electromagnet may be provided to generate a magnetic field that can be used to control the viscosity of the field-responsive fluid 106 in a plurality of speed-control device 350A. FIG. 6E is an illustration of such an example system 500A using the array 400A and a single field generator 110. As shown by the dashed lines, the field generator 110 may be, but is not required to be, physically connected to the array 400A. In some embodiments, individual speed-control devices 350A or subsets of speed-control devices 350A in the array 400A can be provided with circuitry to allow some level of local control (e.g., via the first pole piece 135A and second pole piece 135B) of a field 111 that is applied more globally.

Figure 6F:
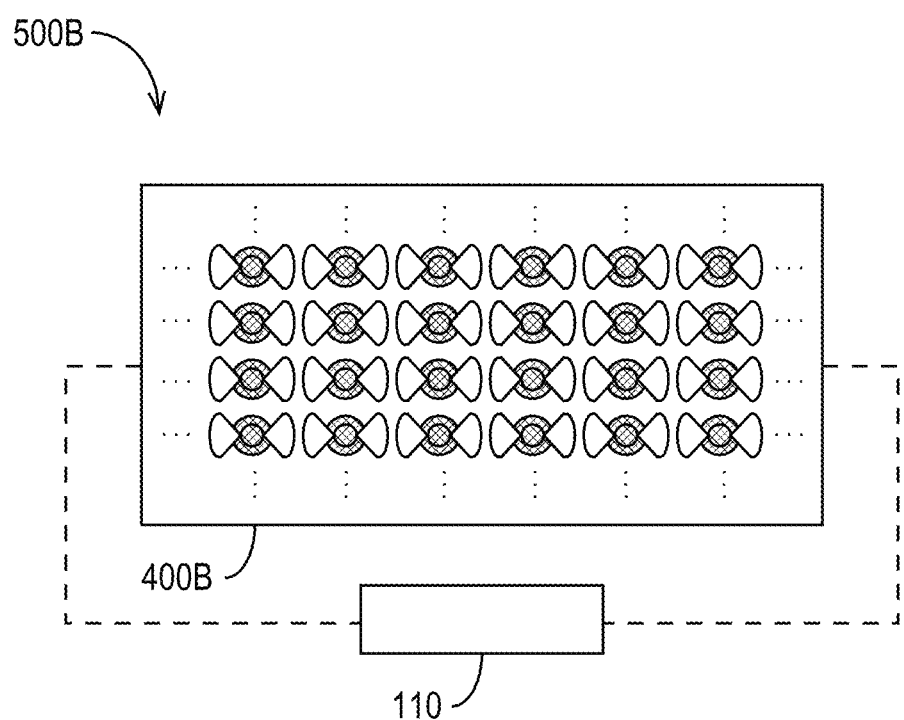
FIG. 6F is an illustration of another example system using an array in accordance with some embodiments.

FIG. 6F is an illustration of another example system 500B using the array 400B and a single field generator 110 to generate a global field. As shown by the dashed lines, the field generator 110 may be, but is not required to be, physically connected to the array 400B. As with the system 500A, the first pole piece 137A and second pole piece 137B of individual speed-control devices 350B in the array 400B of system 500B may allow local tuning of the global field.

In addition, in some embodiments, individual speed-control devices 350B or subsets of speed-control devices 350B in the array 400B can be provided with circuitry to allow some level of local control (e.g., via the first pole piece 137A and second pole piece 137B) of a field 111 that is applied more globally.

Figure 6G:
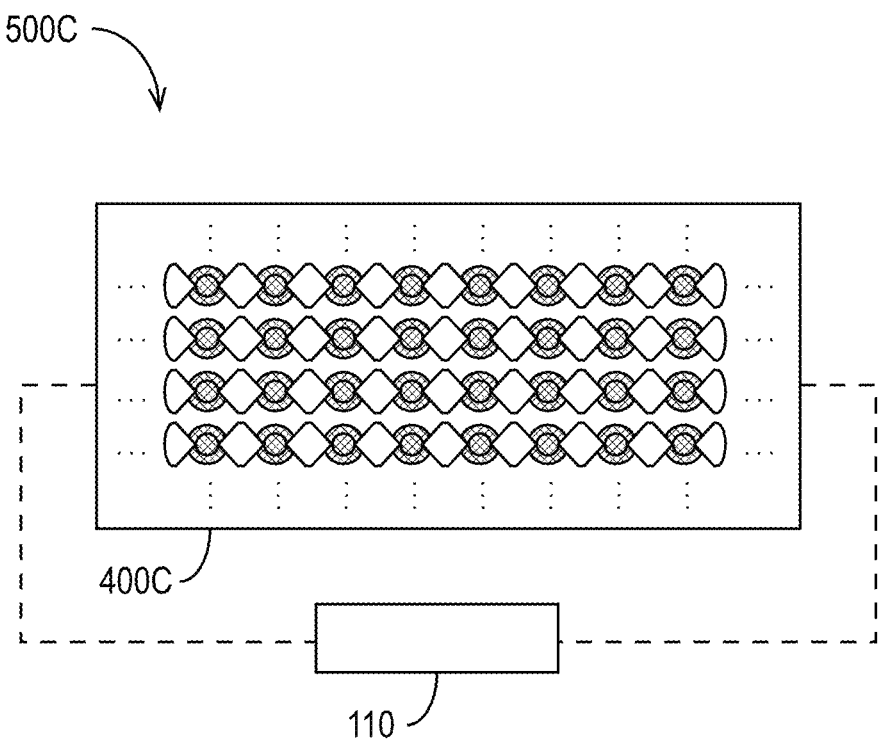
FIG. 6G is an illustration of another example system using an array in accordance with some embodiments.

In some embodiments, neighboring second pole pieces 137B and first pole pieces 137A can be merged to simplify the design and/or fabrication of the system 500B. FIG. 6G is an illustration of another example system 500C using an array 400C and a single field generator 110 to generate a global field. As shown by the dashed lines, the field generator 110 may be, but is not required to be, physically connected to the array 400C. In the rows of the array 400C, neighboring second pole pieces 137B and first pole pieces 137A have been merged. The resulting array 400C may be smaller than a corresponding array 400B with the same number of nanopores 15. Alternatively, the array 400C may be denser than the array 400B as a result of merging neighboring second pole pieces 137B and first pole pieces 137A.

Figure 7:
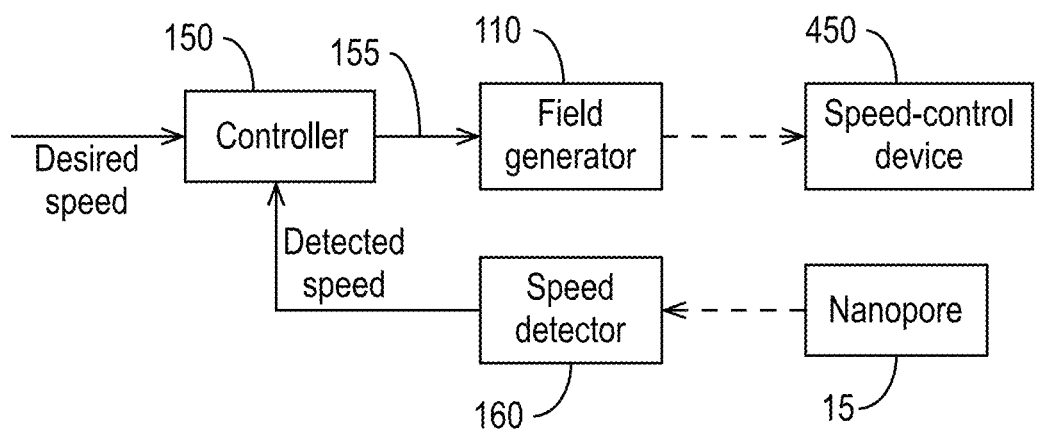
FIG. 7 is a diagram illustrating how feedback can be used to control one or more speed-control devices in accordance with some embodiments.

In some embodiments, a feedback mechanism is provided to allow the applied field 111, whether electric or magnetic, to be tuned during operation in order to adjust the properties (e.g., viscosity) of the field-responsive fluid 106 and, in turn, the translocation speed of a molecule through a nanopore 15. FIG. 7 is a diagram illustrating how feedback can be used to control any of the systems described herein (e.g., by controlling the viscosity of the field-responsive fluid 106) or other similar embodiments of speed-control devices and field generator 110. A speed detector 160 is provided to monitor the speed of molecules (e.g., biomolecules), for example, through a nanopore 15. The speed detector 160 may detect, for example, the highest frequency of the current blockades through a nanopore 15. For example, in the case the biomolecule is DNA, each of the bases (A, T, C, and G) creates a characteristic current blockade (e.g., a "signature"). The frequency at which these characteristic signature blockades are changing can be used to determine whether the translocation speed is too high. The highest frequency detected is inversely proportional to the approximate amount of time each base spends inside the nanopore 15.

The speed detector 160 can provide an indication of the detected translocation speed to a controller 150. The controller 150 can then assess the detected speed (e.g., to determine if it is too high or too low). For example, the controller 150 can compare the detected translocation speed to the desired translocation speed. The desired translocation speed can be, for example, a particular speed or range of speeds providing some desired or target resolution or that causes a biomolecule 20 to spend a desired amount of time within a nanopore 15. The controller 150 may comprise, for example, a differential amplifier that compares the detected translocation speed to the desired translocation speed. The controller 150 can then provide an adjustment signal 155 to the field generator 110 in order to modify the applied field 111. The adjustment signal 155 may be configured to cause the field generator 110 to change some aspect of the applied field 111 (e.g., to increase or decrease the magnitude). As an example, the adjustment signal 155 may cause a voltage provided by a voltage source 121 to be increased or decreased. The applied field then acts on one or more speed-control devices 450, which can be any of the speed-control devices described herein (e.g., in the context of any of FIGS. 2A through 6G), whether or not presented and described using a reference number. For example, the applied field may act on any of speed-control device 250A, speed-control device 350A, or speed-control device 350B, or it may act on or in conjunction with any collection of components that includes at least one fluid-retaining surface 102, a fluid region 105, and a field-responsive fluid 106.

The feedback mechanism of FIG. 7 can be used to control the translocation speed of an individual biomolecule 20 through an individual nanopore 15, or it can be used more globally, such as to adjust the applied field for an array of speed-control devices (e.g., array 400A, array 400B, array 400C, etc.), thereby controlling the viscosities of multiple speed-control devices at once. The controller 150 and speed detector 160 of FIG. 7 can be implemented in any suitable manner, including, for example, by using one or more processors executing machine-executable instructions. Those having ordinary skill in the art will recognize that there are myriad ways to implement the components illustrated in FIG. 7, including in application-specific integrated circuits (ASICs), digital signal processors (DSPs), microprocessors, and similar devices.

Although the disclosure herein is largely in the context of biomolecules, it is to be appreciated that embodiments of the speed-control device and associated systems 100 can be used in other applications. For example, embodiments of the speed-control device can be used to control the speeds of non-biological or inorganic molecules, or structures such as carbon nanotubes, polymer molecules, etc. Accordingly, although many of the drawings illustrate at least one nanopore 15, there is no requirement for the disclosed speed-control devices or systems to be restricted to nanopore applications. The disclosures herein are applicable to any environment in which it is desirable to control the speed at which molecules move (e.g., through a solution). It will be appreciated that the field generator 110 described herein can be used to draw or direct molecules into the fluid region 105 so that they experience the higher viscosity of the field-responsive fluid 106 as compared to surrounding fluid (e.g., an electrolyte or other solution containing the molecule(s) being acted upon by the system 100 or speed-control device).

Thus, generally speaking, disclosed herein are systems 100 for controlling the movement of a molecule (which may be either a biomolecule or a non-biological or inorganic molecule, such as a carbon nanotube or a polymer molecule) in a first fluid (e.g., an electrolyte or other solution) having a first viscosity by providing a fluid region 105 defined by at least one fluid-retaining surface 102, a field-responsive fluid 106 situated in the fluid region 105, and a field generator 110 for generating a magnetic or electric field across the fluid region 105. The fluid region 105 is traversable by the molecule, and the field-responsive fluid has a viscosity that is greater than the first viscosity of the first fluid in response to the magnitude of the magnetic or electric field across the fluid region exceeding a threshold magnitude. The field-responsive fluid 106 is coupled to at least a portion of the at least one fluid-retaining surface 102. In some embodiments, the field generator 110 comprises a voltage source 121.

In some embodiments, a system 100 further includes a speed detector 160 configured to detect the speed of the molecule through the fluid region 105 and a controller 150 coupled to the speed detector 160 and configured to obtain, from the speed detector 160, an indication of the detected speed of the molecule through the fluid region 105, and provide, to the field generator 110, a control signal to adjust a magnitude of the magnetic or electric field 111 across the fluid region 105 based at least in part on the indication of the detected speed of the molecule through the fluid region 105.

In some embodiments, the controller 150 is further configured to compare the detected speed to a desired speed of the molecule through the fluid region 105.

In some embodiments, the field-responsive fluid 106 is an electrorheological fluid, and the system 100 further includes a first electrode 125A and a second electrode 125B, wherein at least one of the first electrode 125A or the second electrode 125B comprises the at least one fluid-retaining surface 102. In some embodiments, the at least one fluid-retaining surface 102 comprises a material with an affinity for the electrorheological fluid.

In some embodiments, the at least one fluid-retaining surface 102 is a magnetorheological fluid or a ferrofluid, and the system 100 further comprises a yoke 133 comprising a base, a first leg, and a second leg, and a solenoid 131 situated around the base of the yoke 133, In some embodiments, at least one of the first leg or the second leg comprises the at least one fluid-retaining surface, and the solenoid 131 is coupled to a voltage source. In some embodiments, the yoke 133 comprises a ferromagnetic material.

In some embodiments, the field-responsive fluid is a magnetorheological fluid or a ferrofluid, and the system 100 includes a hollow cylinder 132 and a solenoid 131 situated around the hollow cylinder 132. In some such embodiments, an interior surface of the hollow cylinder 132 comprises the at least one fluid-retaining surface 102, and the solenoid 131 is coupled to a field generator 110. In some embodiments, the hollow cylinder 132 comprises a ferromagnetic material.

Also disclosed herein are methods of controlling the movement of a molecule, including generating a magnetic or electric field 111 across a fluid region 105 situated in an apparatus (e.g., a chip or flow cell that includes an array of speed-control devices), the fluid region 105 containing a field-responsive fluid 106, wherein a viscosity of the field-responsive fluid 106 is dependent on a magnitude of the generated magnetic or electric field 111, detecting the speed of the molecule through the fluid region 105, and adjusting the magnitude of the magnetic or electric field 111 based at least in part on the detected speed of the molecule through the fluid region 105. In some embodiments, the methods also include adding a fluid containing the molecule to the apparatus. In some embodiments, adjusting the magnitude of the magnetic or electric field 111 based at least in part on the detected speed of the molecule through the fluid region 105 comprises adjusting the magnitude of the magnetic or electric field 111 until the speed of the molecule through the fluid region is substantially zero.

Also disclosed herein are systems 100 for controlling the speeds of molecules, where the systems 100 include a field-responsive fluid 106, means for holding the field-responsive fluid 106 in a pathway of the molecule, and means for generating the applied magnetic or electric field 111 across the field-responsive fluid 106. A property of the field-responsive fluid 106 (e.g., its viscosity) is responsive to an applied magnetic or electric field 111. In some embodiments, a system 100 further includes means for detecting the speed of the molecule through the field-responsive fluid 106. In some embodiments, a system 100 also includes means for adjusting the applied magnetic or electric field 111 across the field-responsive fluid 106 in response to the detected speed. In some embodiments, a system 100 also includes means for directing the molecule into the field-responsive fluid 106.

In some embodiments, in response to the magnitude of the applied magnetic or electric field 111 exceeding a threshold, the viscosity of field-responsive fluid 106 is greater than a viscosity of a surrounding fluid (e.g., a fluid, such as an electrolyte or other solution, that contains the molecule being acted on by the system 100).

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to."

The terms "exemplary" and "embodiment" are used to express examples, not preferences or requirements.

The term "coupled" is used herein to express a direct connection/attachment as well as a connection/attachment through one or more intervening elements or structures.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature. As used herein, a feature that is "adjacent" to another feature is in contact with that other feature.

The term "substantially" is used to describe a structure, configuration, dimension, etc. that is largely or nearly as stated, but, due to manufacturing tolerances and the like, may in practice result in a situation in which the structure, configuration, dimension, etc. is not always or necessarily precisely as stated.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

The invention claimed is:

1. A system for controlling a translocation speed of a molecule through a nanopore, the system comprising:
   the nanopore;
   a speed-control device comprising:
      at least one fluid-retaining surface,
      a fluid region, and
      a field-responsive fluid coupled to the at least one fluid-retaining surface and situated in the fluid region; and
   a field generator for generating a magnetic or electric field across the fluid region,
   wherein a viscosity of the field-responsive fluid is dependent on a magnitude of the magnetic or electric field across the fluid region.

2. The system recited in claim 1, wherein the field generator comprises at least one of a voltage source or a switch.

3. The system recited in claim 1, further comprising:
   a speed detector configured to detect a speed of the molecule through the nanopore;
   a controller coupled to the speed detector and configured to:
      obtain, from the speed detector, an indication of the detected speed of the molecule through the nanopore, and
      provide, to the field generator, a control signal to adjust a magnitude of the magnetic or electric field across the fluid region based at least in part on the indication of the detected speed of the molecule through the nanopore.

4. The system recited in claim 3, wherein the controller is further configured to compare the detected speed to a desired speed of the molecule through the nanopore.

5. The system recited in claim 1, wherein the field-responsive fluid is an electrorheological fluid, and further comprising a first electrode and a second electrode, wherein at least one of the first electrode or the second electrode comprises the at least one fluid-retaining surface.

6. The system recited in claim 5, wherein the at least one fluid-retaining surface comprises a material with an affinity for the electrorheological fluid.

7. The system recited in claim 5, further comprising a shield situated between the nanopore and the first and second electrodes.

8. The system recited in claim 1, wherein the field-responsive fluid is a magnetorheological fluid or a ferrofluid.

9. The system recited in claim 8, further comprising a ferromagnetic yoke, wherein the ferromagnetic yoke comprises a base.

10. The system recited in claim 9, further comprising:
    a solenoid situated around the base of the ferromagnetic yoke, wherein the solenoid is coupled to a voltage source.

11. The system recited in claim 8, further comprising:
    a hollow cylinder; and
    a solenoid situated around the hollow cylinder,
    wherein:
      an interior surface of the hollow cylinder comprises the at least one fluid-retaining surface, and
      the solenoid is coupled to a voltage source.

12. The system recited in claim 11, wherein the hollow cylinder comprises a ferromagnetic material.

13. The system recited in claim 1, wherein the speed-control device is situated on a leading side of the nanopore.

14. The system recited in claim 13, wherein the speed-control device and the nanopore are adjacent.

15. The system recited in claim 1, wherein the speed-control device is situated on a trailing side of the nanopore.

16. The system recited in claim 15, wherein the speed-control device and the nanopore are adjacent.

17. A system for reading molecules, the system comprising:
   a plurality of fluid regions, each of the plurality of fluid regions containing a respective volume of field-responsive fluid, each of the plurality of fluid regions corresponding to a respective one of a plurality of nanopores; and
   at least one field generator, the at least one field generator configured to subject the plurality of fluid regions to one or more electric or magnetic fields.

18. The system recited in claim 17, wherein the field-responsive fluid is an electrorheological fluid, and wherein the plurality of fluid regions is arranged in an array, and wherein each of the plurality of fluid regions is associated with a respective pair of electrodes coupled to the at least one field generator.

19. The system recited in claim 17, wherein the field-responsive fluid is a magnetorheological fluid or a ferrofluid, and wherein the plurality of fluid regions is arranged in an array, and wherein each of the plurality of fluid regions is situated between a respective pair of pole pieces.

20. The system recited in claim 19, wherein the plurality of fluid regions comprises a first fluid region and a second fluid region, and wherein the first fluid region is situated between a first pole piece and a second pole piece, and wherein the second fluid region is situated between the second pole piece and a third pole piece.

21. The system recited in claim 19, wherein each of the respective pair of pole pieces comprises a ferromagnetic material.

22. The system recited in claim 17, further comprising:
   a controller coupled to the at least one field generator and configured to adjust the one or more electric or magnetic fields based at least in part on a detected translocation speed.

23. The system recited in claim 22, further comprising:
   a speed detector configured to detect a translocation speed of a molecule and to provide an indication of the detected translocation speed to the controller.

24. The system recited in claim 23, wherein the speed detector is configured to detect the translocation speed of the molecule by recognizing a particular pattern in the molecule.

25. A system for controlling a speed of a molecule through a nanopore, the system comprising:
   means for holding a field-responsive fluid in a pathway of the molecule;
   means for generating a magnetic or electric field across the field-responsive fluid;
   means for detecting a translocation speed of the molecule through the nanopore; and
   means for adjusting the magnetic or electric field across the field-responsive fluid in response to the detected translocation speed.

* * * * *